US011214865B2

(12) United States Patent
Johansson et al.

(10) Patent No.: US 11,214,865 B2
(45) Date of Patent: Jan. 4, 2022

(54) APPARATUS FOR COATING PARTICLES

(71) Applicant: Nanexa AB, Uppsala (SE)

(72) Inventors: Anders Johansson, Uppsala (SE); Mårten Rooth, Uppsala (SE); Joel Hellrup, Uppsala (SE)

(73) Assignee: Nanexa AB, Uppsala (SE)

( * ) Notice: Subject to any disclaimer, the term of this patent is extended or adjusted under 35 U.S.C. 154(b) by 0 days.

(21) Appl. No.: 16/912,599

(22) Filed: Jun. 25, 2020

(65) Prior Publication Data

US 2020/0407846 A1 Dec. 31, 2020

(30) Foreign Application Priority Data

Jun. 28, 2019 (GB) ..................................... 1909314
Dec. 4, 2019 (GB) ..................................... 1917727

(51) Int. Cl.
*C23C 16/455* (2006.01)
*A61J 3/00* (2006.01)
*B01J 2/00* (2006.01)
*B05B 7/00* (2006.01)
*C23C 16/54* (2006.01)
*C23C 16/44* (2006.01)
(Continued)

(52) U.S. Cl.
CPC ......... *C23C 16/45544* (2013.01); *A61J 3/005* (2013.01); *B01J 2/006* (2013.01); *B01J 13/04* (2013.01); *B05B 7/0037* (2013.01); *C23C 16/4412* (2013.01); *C23C 16/54* (2013.01); *A61K 9/501* (2013.01)

(58) Field of Classification Search
CPC ............ C23C 16/45544; C23C 16/442; C23C 16/45555; C23C 16/4412
See application file for complete search history.

(56) References Cited

U.S. PATENT DOCUMENTS

| 5,753,023 | A | 5/1998 | Bishop |
| 6,149,785 | A | 11/2000 | Makowiecki et al. |
| 6,613,383 | B1 | 9/2003 | George et al. |

(Continued)

FOREIGN PATENT DOCUMENTS

| CN | 108220917 A | * | 6/2018 |
| WO | WO-03/008186 A1 | | 1/2003 |
| WO | WO-2019/120593 A1 | | 6/2019 |

OTHER PUBLICATIONS

Arruebo, "Drug delivery from structured porous inorganic materials", WIREs Nanomedicine and Nanobiotechnology, al. 4, Jan./Feb. 2012, pp. 16-30.

(Continued)

*Primary Examiner* — Dah-Wei D. Yuan
*Assistant Examiner* — Stephen A Kitt
(74) *Attorney, Agent, or Firm* — Foley & Lardner LLP

(57) ABSTRACT

A reactor for forming fully coated particles having a solid core, the reactor comprises a reactor vessel which is configured to receive particles, and a gas phase coating mechanism that is configured to selectively introduce pulses of gas phase materials that form a coating on the particles. The reactor also includes a sieve (16) that is located within the reactor vessel, and a forcing means that is configured to force the particles through the sieve (16) in use. The sieve is configured to deagglomerate any particle aggregates formed in the reactor vessel upon forcing of the particles by the forcing means through the sieve.

26 Claims, 12 Drawing Sheets

(51) Int. Cl.
  *B01J 13/04*   (2006.01)
  *A61K 9/50*    (2006.01)

(56) References Cited

U.S. PATENT DOCUMENTS

| | | | |
|---|---|---|---|
| 6,713,177 B2 | 3/2004 | George et al. | |
| 6,913,827 B2 | 7/2005 | George et al. | |
| 7,459,145 B2 | 12/2008 | Bao et al. | |
| 7,678,429 B2 | 3/2010 | Goodwin et al. | |
| 7,684,292 B2 | 3/2010 | Suh et al. | |
| 7,858,144 B2 | 12/2010 | Freeman et al. | |
| 8,097,742 B2 | 1/2012 | Ying et al. | |
| 8,426,489 B1 | 4/2013 | Al-Haik et al. | |
| 10,166,198 B2 | 1/2019 | Carlsson et al. | |
| 10,478,402 B2 | 11/2019 | Carlsson et al. | |
| 10,603,284 B2 | 3/2020 | Hoppu et al. | |
| 2005/0158480 A1 | 7/2005 | Goodwin et al. | |
| 2007/0061006 A1 | 3/2007 | Desatnik et al. | |
| 2007/0238311 A1 | 10/2007 | Levy | |
| 2007/0275853 A1 | 11/2007 | Shichibe et al. | |
| 2009/0186068 A1 | 7/2009 | Miller et al. | |
| 2009/0324676 A1 | 12/2009 | Hofmann et al. | |
| 2010/0016443 A1 | 1/2010 | Toledano et al. | |
| 2011/0022160 A1 | 1/2011 | Flanagan et al. | |
| 2011/0054633 A1 | 3/2011 | Miller et al. | |
| 2011/0104073 A1 | 5/2011 | Zeng et al. | |
| 2011/0229580 A1 | 9/2011 | Srivastava et al. | |
| 2011/0262506 A1 | 10/2011 | Ofer et al. | |
| 2012/0116814 A1 | 5/2012 | Lorsch | |
| 2012/0201860 A1 | 8/2012 | Weimer et al. | |
| 2012/0301720 A1 | 11/2012 | Wieland et al. | |
| 2013/0059073 A1 | 3/2013 | Jiang et al. | |
| 2013/0337056 A1 | 12/2013 | Lehtonen et al. | |
| 2015/0125599 A1* | 5/2015 | Lindfors | C23C 16/45555 427/213 |
| 2015/0132396 A1 | 5/2015 | Coulter et al. | |
| 2015/0250731 A1 | 9/2015 | Hoppu et al. | |
| 2016/0081945 A1 | 3/2016 | Carlsson et al. | |
| 2018/0221294 A1 | 8/2018 | Carlsson et al. | |
| 2019/0046632 A1 | 2/2019 | Randolph et al. | |
| 2019/0216742 A1 | 7/2019 | Neikirk et al. | |
| 2020/0024736 A1 | 1/2020 | Gangakhedkar et al. | |
| 2020/0108023 A1 | 4/2020 | Carlsson et al. | |

OTHER PUBLICATIONS

Dillon et al., "Surface chemistry of Al2O3 deposition using Al(CH3)3 and H2O in a binary reaction sequence", Surface Science 322, 1995, pp. 230-242.
Guo et al., "GaN Nanowire Functionalized with Atomic Layer Deposition Techniques for Enhanced Immobilization of Biomolecules", Langmuir Article, vol. 26, No. 23, 2010, pp. 18382-18391.
Hakim et al., "Conformal nanocoating of zirconia nanoparticles by atomic layer deposition in a fluidized bed reactor", Nanotechnology, vol. 16, 2005, pp. S375-S381.
Abstract of Herrera A.P et al., J. Mater. Chem., 2008, 18 pp. 3650-3654, "Synthesis and functionalization of magnetite nanoparticles with aminopropylsilane and carboxymethyldextran", Available at https://pubs.rsc.org/en/content/articlelanding/2008/jm/b805256e#!divAbstract.
Hyde et al., "Atomic layer deposition of titanium dioxide on cellulose acetate for enhanded hemostasis", Biotechnology Journal, vol. 6, 2011, pp. 113-223.
Knez et al., "Atomic Layer Deposition on Biological macromolecules: Metal Oxide Coating of Tobacco Mosaic Virus and Ferritin", Nano Letters, vol. 6, No. 6, 2006, pp. 1172-1177.
Korhonen et al., "Inorganic Hollow Nanotube Aerogels by Atomic Layer Deposition onto Native Nanocellulose Templates", ACS Nano, vol. 5, No. 3, 2011, pp. 1967-1974 (8 pages).
Kumaresan et al., "Dry Powder Inhaler—Formulation aspects", Pharma Times, vol. 44, No. 10, Oct. 2012, pp. 14-18 (5 pages).
Lee et al., "Low-temperature ZnO atomic layer deposition on biotemplates: flexible photocatalytic ZnO structures from eggshell membranes", Physical Chemistry Chemical Physics, vol. 11, 2009, pp. 3608-3614 (7 pages).
Lin et al., "CVD of Solid Oxides in Porous Substrates for Ceramic Membrane Modification", AIChE Journal, vol. 38, No. 3, pp. 445-454 (10 pages).
Mack et al., "Particle engineering for inhalation formulation and delivery of biotherapeutics", Inhalation, vol. 6, No. 4, Aug. 2012, pp. 16-20 (5 pages).
Ott et al., "Al3O3 thin film growth on Si(100) using binary reaction sequence chemistry", Thin Solid Films 292, 1997, pp. 135-144 (10 pages).
Sivasankar et al., "Role of Nanoparticles in Drug Delivery System", International Journal of Research in Pharmaceutical and Biomedical Sciences, vol. 1 (2), Dec. 2010, pp. 41-66 (26 pages).
Tsapatsis et al., "Synthesis of Hydrogen Permselective SiO2, TiO2, Al2O3, and B2O3 Membranes from the Chloride Precursors", Ind. Eng. Chem. Research, vol. 30, No. 9, 1991, pp. 2152-2159 (8 pages).
Van Ommen et al., "Fluidization of nanopowders: a review", J Nanopart Res, 2012, 14:737, pp. 1-29 (29 pages).
Zarie et al. "Solvent Free Fabrication of Micro and Nanostructured Drug Coatings by Thermal Evaporation for Controlled Release and Increased Effects", PLoS ONE, 2012, 7(8):40746 (11 pages).
Abstract of CN-102330051-A (Li et al.)—published Jan. 25, 2012.
Abstract of JP-2010-006780-A (Tsukioka KK)—published Jan. 14, 2010.
Abstract of JP-2010-059005-A (Kanazawa Inst of Technology, Nat Inst for Materials Science)—published Mar. 18, 2010.
Declaration of Anders Johansson Under 37 C.F.R. ?1.132 submitted in co-owned U.S. Appl. No. 15/944,059.
Feil et al., "Nanoparticle based inorganic coatings for corrosion protection of magnesium alloy," Surface Engineering 24.3, 2008), pp. 198-203.
First Office Action issued in Nanexa co-owned U.S. Appl. No. 15/944,059.
Notice of Allowance issued in Nanexa co-owned U.S. Appl. No. 15/944,059.
Picosun Oy, Picosun enables ALD on Powders.
Picosun Oy, Picosun SUNALE™ R-series.
Raula et al. "A novel gas phase method for the combined synthesis and coating of pharmaceutical particle", Pharmaceutical Research 25.1, 2007, pp. 242-245 (4 pages).
Third Party Submission filed in Nanexa co-owned U.S. Appl. No. 14/891,398.
Adhikari Sangeeta et al.: "Progress in Powder Coating Technology Using Atomic Layer Deposition", Advanced Materials Interfaces, Wiley-V C H Verlag Gmbh & Co. KGAA, DE, vol. 5, No. 16 Aug. 1, 2018 (Aug. 1, 2018), p. 1800581 ,XP009522071,ISSN: 2196-7350, DOI:10.1002/ADMI .201800581 Retrieved from the Internet: URL:https: //api.wiley.com/onlinelibrary/tdm/vl/articles/10.1002%2Fadmi.201800581 [retrieved on Jul. 18, 2018].
D. Zhang et al.: "Atomic scale surface engineering of micro- to nano-sized pharmaceutical particles for drug delivery applications", NANOSCALE vol. 9, No. 32. Jan. 1, 2017 (Jan. 1, 2017), pp. 11410-11417, XP055719743, United Kingdom ISSN: 2040-3364, Doi: 10.1039/C7NR03261G A Fig. 1, Tables 1,2 p. 11411 third paragraph, p. 11410 last paragraph, section "Conclusions".
Duan Chen-Long et al.: "Surface passivation of Fe3O4 nanoparticles with Al 2O3via atomic layer deposition in a rotating fluidized bed reactor", Journal of Vacuum Science and Technology: Part A, AVS /AIP, Melville, NY., US, vol. 34, No. 4, May 23, 2016 (May 23, 2016),XP012207942,ISSN: 0734-2101, DOI : 10 . 1116/1.4952401.
International Search Report on PCT/GB2020/051177 dated Aug. 14, 2020.

* cited by examiner

APPARATUS FOR COATING PARTICLES

CROSS-REFERENCE TO RELATED APPLICATIONS

This application claims the benefit of and priority to Great Britain Patent Application No. 1909314.5, filed Jun. 28, 2019, and also to Great Britain Patent Application No. 1917727.8, filed Dec. 4, 2019, the entire contents of both of which are incorporated herein by reference.

TECHNICAL FIELD

This invention relates to a reactor for forming fully coated particles having a solid core, a method of forming such fully coated particles and to a plurality of fully coated particles. The invention also relates to a pharmaceutical composition comprising a pharmacologically-effective amount of a biologically active agent in the form of such fully coated particles and to a pharmaceutical or veterinary formulation comprising such a pharmaceutical composition.

BACKGROUND

It is known to apply a coating to a substance using a gas phase coating technique, such as atomic layer deposition (ALD). The gas phase coating technique sequentially introduces pulses of gas phase materials or reactants to deposit or form a coating on the substance. In many gas phase coating techniques, it is pulses of precursor gases that are sequentially introduced. The precursor gases react with each other on the surface of the substance, thus "growing" a coating onto the substance. Several pulses of gas phase materials can be applied to form a coating of a desired thickness and composition.

As an example, the steps taken in an ALD technique are generally as follows:

a) Adding a first precursor in the gaseous state to a reaction chamber containing the substrate to be coated, which precursor being thereby adsorbed onto the surface of the substrate;

b) Removing excess of the first precursor from the reaction chamber by purging and/or evacuating the reactor;

c) Adding a second precursor, which reacts with the first precursor on the surface of the substrate, thus creating a new layer of a different chemical composition on the surface of the substrate; and d) Removing excess of the second precursor and any by-products by purging/evacuating the reactor.

Steps a) to d), which may be referred to as a "cycle" of pulses of evaporated or gaseous precursors, may then be repeated in order to achieve the desired coating thickness. More than two precursors can also be used.

The inventors previously found that, when applying such gas phase coating techniques to a plurality of particles, particularly drug particles on the micro- or nano-meter scale, the particles have a tendency to clump together to form aggregates (may also be referred to as agglomerates) of particles. The particles in the aggregates will not be fully exposed to the gas phase materials. An incomplete coating is therefore formed around the particles in the aggregates because, once they are separated after the gas phase coating technique is complete, small contact spots or pinholes are created in the coating of the particles where the particles were once clumped together. Thus, the core of the coated particle is left exposed.

The core of the coated particle being left exposed is particularly problematic where the core comprises a drug and the coating provides a means for a controlled release of that drug. In the field of drug delivery, the ability to control the profile of drug release is of critical importance. It is desirable to ensure that active ingredients provide for release of that active ingredient at a desired and predictable rate in vivo following administration, in order to ensure the optimal pharmacokinetic profile. The core of a coated particle used for controlled release of a drug being left exposed means that the drug core may be quickly dissolved as soon as it contacts a release medium, thus resulting in nearly instantaneous release of parts of the drug (so-called "burst release"). Burst release may be hazardous in the case of drugs that have a narrow therapeutic window.

Moreover, if the aggregates are not separated into particles of a desired size then the resultant coated particles have an uneven size distribution. In particular, there would be large coated aggregates present which is highly undesirable when the particles are being used in a pharmaceutical composition. In the case of a pharmaceutically-acceptable injectable suspension of coated drug particles, the size of the particles must be controlled so that they can be injected through a needle. Larger, aggregated particles will not only block the needle through which the suspension is to be injected, but also will not form a stable suspension because the large aggregates will not be properly suspended (they will instead tend to sink to the bottom of the injection liquid).

SUMMARY

According to a first aspect of the invention there is provided a reactor for forming a plurality of fully coated particles having a solid core, the reactor comprising:
a reactor vessel configured to receive particles;
a gas phase coating mechanism configured to selectively introduce pulses of gas phase materials that form a coating on the particles;
a sieve located within the reactor vessel; and
a forcing means configured to force the particles through the sieve in use,
wherein the sieve is configured to deagglomerate any particle aggregates formed in the reactor vessel upon forcing of the particles by the forcing means through the sieve.

It will be understood that the term "fully coated" means that the coating absolutely covers whole solid cores of essentially all particles, such that no pinholes or contact spots are present. The coating is therefore a dense shell that fully encloses the solid core. In other words, the coating is essentially free of abrasions, pinholes, breaks, gaps, cracks and/or voids through which the solid core underneath the coating is potentially exposed.

The term "solid" will be well understood by those skilled in the art to include any form of matter that retains its shape and density when not confined, and/or in which molecules are generally compressed as tightly as the repulsive forces among them will allow. The solid cores have at least a solid exterior surface onto which a coating can be deposited. The interior of the solid cores may be also solid or may instead be hollow. For example, if the particles are spray dried before they are entered into the reactor vessel, they may become hollow due to the spray drying technique.

The inclusion of a sieve as outlined above means that the particle aggregates are broken up by the forcing means forcing them through the sieve, thus separating the aggregates into individual particles or aggregates of a desired and predetermined size (thereby achieving deagglomeration). In the latter regard, in some cases the individual primary particle size is so small (i.e. <1 μm) that achieving "full" deagglomeration (i.e. where aggregates are broken down into individual particles) is not possible. Instead, deagglomeration is achieved by breaking down larger aggregates into smaller aggregates of secondary particles of a desired size, as dictated by the size of the sieve mesh. The smaller aggregates are then coated by the gas phase technique to form fully coated "particles" in the form of small aggregate particles. In this way, the term "particles", when referring the particles that have been deagglomerated and coated in the context of the invention, refers to both individual (primary) particles and aggregate (secondary) particles of a desired size.

In any event, the desired particle size (whether that be of individual particles or aggregates of a desired size) is maintained and, moreover, continued application of the gas phase coating mechanism to the particles after such deagglomeration via the sieve means that a complete coating is formed on the particle, thus forming fully coated particles (individual or aggregates of a desired size).

Meanwhile, having the sieve located within the reactor vessel means that the coating can be applied by way of a continuous process which does not require the particles to be removed from the reactor. Thus, no manual handling of the particles is required, and no external machinery is required to deagglomerate the aggregate particles. This not only considerably reduces the time of the coating process being carried out, but is also more convenient and reduces the risk of harmful (e.g. poisonous) materials being handled by personnel. It also enhances the reproducibility of the process by limiting the manual labour and reduces the risk of contamination.

As an example, the inventors previously found that extracting particles comprising a drug core from a gas phase technique reactor and manually deagglomerating them in between sets of the gas phase technique cycles was successful in producing fully coated particles (see WO 2014/187995). However, each batch of particles could take several days to fabricate. Moreover, the manual steps of removing the particles were not only potentially harmful because of the potential presence of toxic primary ingredients, but also required a very clean environment (e.g. cleanroom facilities), which adds considerable cost to the manufacture process.

The forcing means may take any suitable form which forces the particle aggregates through the sieve with enough force to break the connection between the particles so as to achieve deagglomeration. For example, the forcing means may be or may include: shaking, tapping, oscillating, tumbling, horizontal rotation, periodical displacement of the sieve, centrifugal force, sonic vibration, ultrasonic vibration, vacuum, air column, pressure gradient, gas flow, brushing, gravitational or a combination thereof. Such combinations may include, but are not limited to, the following: oscillating and tapping, rotating and tapping, ultrasonic and sonic vibration, sonic vibration and tapping, ultrasonic vibration and tapping.

In some instances, the forcing means may be instead of or in addition to gravitational force.

Preferably the forcing means is integrated with the reactor vessel and is, or includes, sonic vibration such that the vessel and sieve act as a sonic sifter.

Optionally the forcing means includes a forcing aid to aid in forcing the particles through the sieve in use.

The inclusion of such a forcing aid helps to apply sufficient force of the particle aggregates through the sieve to achieve deagglomeration. The forcing aid can also help to speed up achieving deagglomeration of the particles.

The forcing aid may take any suitable form, and in particular may be or include: brush, balls, scraper, spatula, paddle, air jet, or a combination thereof.

Optionally the ratio of the size of particles to the sieve mesh size is about 1:>1. Preferably, the ratio is about 1:2, and optionally it is about 1:4.

The inventors found that this ratio is able to break up the particle aggregates sufficiently to achieve deagglomeration while permitting the single particles to pass through the sieve.

In an embodiment of the invention the reactor further includes a plurality of sieves located within the reactor vessel, each sieve having a progressively finer mesh in the direction of forcible movement of the particles.

The inclusion of such a succession of sieves allows for particle aggregates to be deagglomerated in a step-wise manner. In other words, the largest aggregates may be separated into smaller aggregates first in the largest sieve mesh, and then separated into smaller and smaller aggregates (depending on the number of sieves included in the reactor) until the desired deagglomeration is achieved by the final smallest mesh sieve. Sieving can also be stopped to achieve agglomerates of a desired size. Such step-wise deagglomeration may require less force from the forcing means at each sieving step, thus saving energy used by the reactor and process time, as well as being gentler to the particles and formed coating.

Preferably the reactor vessel includes more than one reactor chamber, with sieves being located between neighbouring reactor chambers, the gas phase coating mechanism being configured to selectively introduce one or more pulses of gas phase materials, such as reactants or precursors, to the particles in one or each reactor chamber.

The inclusion of more than one reactor chamber and the gas phase coating mechanism being configured as outlined above means that different pulses of gas can be introduced to the particles in the different chambers, if desirable. Moreover, the sieve being located between each neighbouring reactor chamber means that deagglomeration can be achieved between stages of the gas phase coating mechanism.

The reactor may further include a particle position-changing means configured to action movement of the particles from one physical space in the reactor to another to permit subsequent forcing of the particles through the sieve.

The inclusion of such a particle position-changing means allows further exposure to gas phase materials and subsequent forcing of the particles through the sieve. As such, these steps can be repeated in the reactor a desired number of times, e.g. to achieve a desired thickness of coating.

In an embodiment of the invention, the particle position-changing means may be a movement member configured to physically move each of the reactor chambers so as to switch places of the reactor chambers.

The inclusion of a movement member which is configured to physically move each reactor chamber means that the particles can remain inside the chamber throughout the process, which may be desirable depending on the nature of the particles and/or coating materials.

The size and number of the reactor chambers, as well as the space available to house the reactor, may dictate how the reactor chambers are physically moved.

For example, the movement member may be configured to rotate the reactor chambers along a single axis to switch places of the reactor chambers.

Alternatively, the movement member may be configured to switch the places of the reactor chambers without rotation of the reactor chambers.

Preferably each reactor chamber includes a sieve located on an intermediate surface, the intermediate surface being located between neighbouring reactor chambers upon switching of their places so that a sieve is located between the reactor chambers at any given time.

A sieve being located on such an intermediate surface means that a sieve is readily available for carrying out deagglomeration after the reactor chambers have switched places without the need for, e.g. an external sieve which would need to be repositioned between neighbouring reactor chambers after each time they have switched places.

In another embodiment of the invention, the particle position-changing means may be a particle transport mechanism configured to transport the particles between each of the reactor chambers.

The inclusion of a particle transport mechanism which is configured to transport the particles between each of the reactor chambers means that the reactor chambers themselves do not need to be physically moved, which may be desirable if the available space for the reactor to operate in is limited. It may also result in a less complex design of the gas phase coating mechanism since it can be operatively coupled to the reactor throughout operation.

The particle transport mechanism may be or may include: an airflow, a fluidised bed, a vacuum, a physical transportation mechanism (such as a conveyor belt), or a combination thereof or other means knowns for a person skilled in the art.

In a further embodiment of the invention, the particle position-changing means may include a movement member as described hereinabove and a particle transport mechanism as described hereinabove.

In this way, the particles can be moved around the reactor by a combination of physically moving the reactor chambers and moving the particles between the reactor chambers.

In any event, the reactor may further include a stop means positioned relative to the, or each, sieve to selectively prevent passing of the particles through the sieve into a neighbouring reactor chamber. The stop means may be or may include: a physical stop, an airflow, or a combination thereof.

The inclusion of such a stop means permits control of the particles passing through the sieve and into a neighbouring reactor chamber. It may also help to create a sealed reactor chamber for when the gas phase coating mechanism is in operation.

The forcing means may be configured to force the particles through the sieve after each pulse of gas phase materials provided by the gas phase coating mechanism.

The forcing means being so configured means that consecutive pulses of gas can be applied in each reactor chamber with the particles being forced through the sieve between each pulse. Thus, since deagglomeration is carried out frequently throughout operation of the reactor, the operation time to achieve the fully coated particles may be less.

Alternatively, the forcing means may be configured to force the particles through the sieve after a plurality of pulses or cycles of gas phase materials provided by the gas phase coating mechanism.

The forcing means being so configured means that more than one step of the gas phase coating can be performed in a single reactor chamber, with the particles being forced through the sieve between each stage. Such a frequency of deagglomeration may be suitable for some particles and/or gas phase materials. Moreover, the footprint of the reactor may be smaller due to less reactor chambers being required to carry out the repeatable gas phase coating steps.

The gas phase coating mechanism may incorporate one of the following gas phase coating techniques: atomic layer deposition (ALD), atomic layer epitaxy (ALE), molecular layer deposition (MLD), molecular layer epitaxy (MLE), chemical vapor deposition (CVD), atomic layer CVD, molecular layer CVD, physical vapor deposition (PVD), sputtering PVD, reactive sputtering PVD, evaporation PVD, binary reaction sequence chemistry.

Such techniques are known in the art of gas phase coating and the components required to incorporate these techniques into the gas phase coating mechanism would be apparent to a person skilled in this art.

According to second aspect of the invention there is provided a method of forming a plurality of fully coated particles comprising the steps of:
  i) providing a plurality of particles into a gas phase coating reactor;
  ii) subjecting those particles to pulses of gas phase materials by a gas phase coating technique so as to coat the particles;
  iii) forcing the particles through a sieve within the reactor to deagglomerate any particle aggregates formed during step ii); and
  iv) repeating steps ii) and iii) to form particles with solid cores, the solid cores being fully enclosed by coatings formed by the gas phase coating technique.

The advantages of the reactor of the first aspect of the invention and its embodiments applies mutatis mutandis to the method of the second aspect of the invention and its embodiments.

This repeated coating and deagglomeration process (i.e. steps ii) and iii)) may be carried out at least 1, preferably 2, more preferably 3, such as 4, including 5, more particularly 6, e.g. 7 times, and no more than about 100 times, for example no more than about 50 times, such as no more than about 40 times, including no more than about 30 times, such as between 2 and 20 times, e.g. between 3 and 15 times, such as 10 times, e.g. 9 or 8 times, more preferably 6 or 7 times, and particularly 4 or 5 times.

Optionally step ii) includes applying a single cycle of pulses of gas phase materials to form an initial layer of a coating on the particles and step iii) includes forcing the particles through the sieve after each cycle of pulses of gas phase materials applied in step ii).

Thus, the particles are forced through the sieve between each cycle of pulses of the gas phase technique, and so frequent deagglomeration is carried out throughout the method.

According to a third aspect of the invention there is provided a plurality of fully coated particles comprising:
  a plurality of particles each having a solid core, the solid core being fully enclosed by a coating, the plurality of fully coated particles being prepared according to a method comprising the steps of:
  i) providing a plurality of particles into a gas phase coating reactor;
  ii) subjecting those particles to pulses of gas phase materials by a gas phase coating technique so as to coat the particles;

iii) forcing the particles through a sieve within the reactor to deagglomerate any particle aggregates formed during step ii); and iv) repeating steps ii) and iii) to form particles with solid cores, the solid cores being fully enclosed by the coating formed by the gas phase coating technique.

The advantages of the reactor of the first aspect of the invention and its embodiments applies mutatis mutandis to the plurality of fully coated particles of the third aspect of the invention and its embodiments.

Moreover, the provision of a plurality of fully coated particles in accordance with the third aspect of the invention provides particles with substantially uniform size, i.e. about the same size, and with minimal exposure of the solid core through the coating in the form of pinholes, or the like, in the coating. As outlined above in the introductory portion of the application, such features are particularly advantageous when the particles are being used in a pharmaceutical composition.

In addition to the foregoing, the inventors have found that if the particles are removed from the reactor during the coating process and deagglomerated outside of the reactor, then the outermost surface of the coated particles takes on a visibly (when analysed using transmission electron microscopy (TEM)) different physical character compared to what lies beneath it. Thus, giving rise to visible (by TEM) interfaces between separate coating layers of, e.g. metal oxides, similar to rings in the cross-section of the trunk of a tree. The interfaces, which are not possible to characterise in terms of their chemical composition, correspond to the time when the coated particles were removed from the reactor and deagglomeration took place.

In contrast, the fully coated particles according to the third aspect of the invention are devoid of any visible distinction between the separate layers of coating from the gas phase coating technique. Instead, the coating is visible (by TEM) only as a single uniform layer having an overall thickness which is related to the number of layers of gas phase material applied by the gas phase coating technique. This is the case even if different gas phase materials are used in the gas phase coating technique. Thus, the particles are distinct in that they are fully coated (i.e. fully encapsulated, with minimal, and/or largely no, pinholes present) and have a visible (by TEM) single uniform coating layer with no interfaces.

The cores may be provided in the form of nanoparticles or, more preferably, microparticles. In this respect, the cores to be coated may be of a size that is of a weight-, number-, or surface area-, based mean diameter that is between about 10 nm and about 50 μm, such as between about 50 nm (e.g. about 100 nm, such as about 250 nm) and about 30 μm, for example between about 500 nm and about 700 μm, such as about 100 μm, more particularly between about 1 μm and about 50 μm, such as about 25 μm, e.g. about 20 μm.

As used herein, the term "weight based mean diameter" will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). As used herein, the term "number based mean diameter" will be understood by the skilled person to include that the average particle size is characterised and defined from a particle size distribution by number, i.e. a distribution where the existing fraction (relative amount) in each size class is defined as the number fraction, as measured by e.g. microscopy. As used herein, the term "surface area based mean diameter" will be understood by the skilled person to include that the average particle size is characterised and defined from a particle size distribution by surface area, i.e. a distribution where the existing fraction (relative amount) in each size class is defined as the surface area fraction, as measured by e.g. laser diffraction. Other instruments that are well known in the field may be employed to measure particle size, such as equipment sold by e.g. Malvern Instruments, Ltd (Worcestershire, UK) and Shimadzu (Kyoto, Japan).

Particles may be spherical, that is they possess an aspect ratio smaller than about 20, more preferably less than about 10, such as less than about 4, and especially less than about 2, and/or may possess a variation in radii (measured from the centre of gravity to the particle surface) in at least about 90% of the particles that is no more than about 50% of the average value, such as no more than about 30% of that value, for example no more than about 20% of that value. The diameter may be between about 1 μm and about 50 μm.

Nevertheless, the coating of particles on any shape is also possible in accordance with the invention. For example, irregular shaped (e.g. "raisin"-shaped), needle-shaped, or cuboid-shaped particles may be coated. For a non-spherical particle, the size may be indicated as the size of a corresponding spherical particle of e.g. the same weight, volume or surface area. Hollow particles, as well as particles having pores, crevices etc., such as fibrous or "tangled" particles may also be coated in accordance with the invention.

Particles may be obtained in a form in which they are suitable to be coated or be obtained in that form, for example by particle size reduction processes (e.g. crushing, cutting, milling or grinding to a specified weight based mean diameter (as hereinbefore defined), for example by wet grinding, dry grinding, air jet milling (including cryogenic micronization), ball milling, such as planetary ball milling, as well as making use of end-runner mills, roller mills, vibration mills, hammer mills, roller mill, fluid energy mills, pin mills, etc. Alternatively, particles may be prepared directly to a suitable size and shape, for example by spray-drying, precipitation, including the use of supercritical fluids or other top-down methods (i.e. reducing the size of large particles, by e.g. grinding, etc.), or bottom-up methods (i.e. increasing the size of small particles, by e.g. sol-gel techniques, etc.). Nanoparticles may alternatively be made by well-known techniques, such as gas condensation, attrition, chemical precipitation, ion implantation, pyrolysis, hydrothermal synthesis, etc.

Moreover, the coating may have a total thickness of between about 0.5 nm and about 2 μm, preferably about 5 nm to about 250, such as about 5 nm to about 100 nm.

Coatings that may be applied to cores comprising active ingredient (as described in more detail below) may be pharmaceutically-acceptable, in that they should be essentially non-toxic.

Coatings may comprise organic or polymeric materials, such as a polyamide, a polyimide, a polyurea, a polyurethane, a polythiourea, a polyesters or a polyimine. Coatings may also comprise hybrid materials (as between organic and inorganic materials), including materials that are a combination between a metal, or another element, and an alcohol, a carboxylic acid, an amine or a nitrile. However, it is preferred that coatings comprise inorganic materials.

Inorganic coatings may comprise one or more metals or metalloids, or may comprise one or more metal-containing, or metalloid-containing, compounds, such as metal, or metalloid, oxides, nitrides, sulphides, selenides, carbonates, and/or other ternary compounds, etc. Metal, and metalloid, hydroxides and, especially, oxides are preferred, especially metal oxides.

Metals that may be mentioned include alkali metals, alkaline earth metals, noble metals, transition metals, post-transition metals. Metal and metalloids that may be mentioned include aluminium, titanium, magnesium, iron, gallium, zinc, zirconium, niobium, hafnium, tantalum, lanthanum, and/or silicon; more preferably aluminium, titanium, magnesium, iron, gallium, zirconium, and/or silicon; especially aluminium, titanium and/or zinc.

Individual coatings may also comprise a mixture of two or more inorganic materials, such as metal oxides or metalloid oxides, and/or may comprise multiple layers or composites of different inorganic or organic materials, to modify the properties of the coating layer.

Coating materials that may be mentioned include those comprising aluminium oxide ($Al_2O_3$), boron oxide ($B_2O_3$) titanium dioxide ($TiO_2$), iron oxides ($Fe_xO_y$, e.g. FeO and/or $Fe_2O_3$ and/or $Fe_3O_4$), gallium oxide ($Ga_2O_3$), magnesium oxide (MgO), zinc oxide (ZnO), niobium oxide ($Nb_2O_5$), hafnium oxide ($HfO_2$), tantalum oxide, scandium oxide ($Sc_2O_3$), yttrium oxide ($Y_2O_3$), indium oxide ($In_2O_3$), thallium oxide ($Ta_2O_5$), lanthanum oxide ($La_2O_3$), zirconium dioxide ($ZrO_2$) and/or silicon dioxide ($SiO_2$). Preferred coating materials include aluminium oxide, titanium dioxide, iron oxides, gallium oxide, magnesium oxide, zinc oxide, zirconium dioxide and silicon dioxide. More preferred coating materials include iron oxide, as well as titanium dioxide, zinc oxide and aluminium oxide.

The solid cores may preferably comprise a biologically active agent. The solid cores may consist essentially of, or comprise, that agent (which agent may hereinafter be referred to interchangeable as a "drug", and "active pharmaceutical ingredient (API)" and/or an "active ingredient"). Biologically active agents also include biopharmaceuticals and/or biologics. Biologically active agents can also include a mixture of different API's, as different API particles or particles comprising more than one API.

By "consists essentially" of biologically-active agent, we include that the solid core is essentially comprised only of biologically active agent(s), i.e. it is free from non-biologically active substances, such as excipients, carriers and the like (vide infra). This means that the core may comprise less than about 5%, such as less than about 3%, including less than about 2%, e.g. less than about 1% of such other excipients.

In the alternative, cores comprising biologically active agent may include such an agent in admixture with one or more pharmaceutical ingredients, which may include pharmaceutically-acceptable excipients, such as adjuvants, diluents or carriers, and/or may include other biologically active ingredients.

Biologically active agents may be presented in a crystalline, a part-crystalline and/or an amorphous state. Biologically active agents may further comprise any substance that is in the solid state, or which may be converted into the solid state, at about room temperature (e.g. about 18° C.) and about atmospheric pressure, irrespective of the physical form. Such agents should also remain in the form of a solid whilst being coated in the reactor and also should not decompose physically or chemically to an appreciable agree (i.e. more than about 10% w/w) whilst being coated, or after having been covered by at least one of the aforementioned coatings. Biologically active agents may further be presented in combination (e.g. in admixture or as a complex) with another active substance.

As used herein, the term "biologically active agent", or similar and/or related expressions, generally refer(s) to any agent, or drug, capable of producing some sort of physiological effect (whether in a therapeutic or prophylactic capacity against a particular disease state or condition) in a living subject, including, in particular, mammalian and especially human subjects (patients).

The cores may instead not comprise a biologically active agent. Whether the cores do or do not comprise a biologically active agent, the cores may comprise and/or consist essentially of a pH modifying agent (e.g. citric acid).

Biologically active agents may, for example, be selected from an analgesic, an anaesthetic, an anti-ADHD agent, an anorectics agent, an antiaddictives agent, an antibacterial agent, an antimicrobial agent, an antifungal agent, an antiviral agent, an antiparasitic agent, an antiprotozoal agent, an anthelminic, an ectoparasiticide, a vaccine, an anticancer agent, an antimetabolite, an alkylating agent, an antineoplastic agent, a topoisomerase, an immunomodulator, an immunostimulant, an immunosuppressant, an anabolic steroid, an anticoagulant agent, an antiplatelets agent, an anticonvulsant agent, an antidementia agent, an antidepressant agent, an antidote, an antihyperlipidemic agent, an antigout agent, an antimalarial, an antimigraine agent, an anti-inflammatory agent, an antiparkinson agent, an antipruritic agent, an antipsoriatic agent, an antiemetic, an anti-obesity agent, an anthelmintic, an anti-arrhythmic agent, an antiasthma agent, an antibiotic, an anticoagulant, an antidepressant, an antidiabetic agent, an antiepileptic, an antifibrinolytic agent, an antihemorrhagic agent, an antihistamine, an antitussive, an antihypertensive agent, an antimuscarinic agent, an antimycobacterial agent, an antioxidant agent, an antipsychotic agent, an antipyretic, an antirheumatic agent, an antiarrhythmic agent, an anxiolytic agent, an aphrodisiac, a cardiac glycoside, a cardiac stimulant, an entheogen, an entactogen, an euphoriant, an orexigenic, an antithyroid agent, an anxiolytic sedative, a hypnotic, a neuroleptic, an astringent, a bacteriostatic agent, a beta blocker, a calcium channel blocker, an ACE inhibitor, a angiotensin II receptor antagonist, a renin inhibitor, a beta-adrenoceptor blocking agent, a blood product, a blood substitute, a bronchodilator, a cardiac inotropic agent, a chemotherapeutic, a coagulant, a corticosteroid, a cough suppressant, a diuretic, a deliriant, an expectorant, a fertility agent, a sex hormone, a mood stabilizer, a mucolytic, a neuroprotective, a nootropic, a neurotoxin, a dopaminergic, an antiparkinsonian agent, a free radical scavenging agent, a growth factor, a fibrate, a bile acid sequestrants, a cicatrizant, a glucocorticoid, a mineralcorticoid, a haemostatic, a hallucinogen, a hypothalamic-pituitary hormone, an immunological agent, a laxative agent, a antidiarrhoeals agent, a lipid regulating agent, a muscle relaxant, a parasympathomimetic, a parathyroid calcitonin, a serenic, a statin, a stimulant, a wakefulness-promoting agent, a decongestant, a dietary mineral, a biphosphonate, a cough medicine, an ophthamological, an ontological, a H1 antagonist, a H2 antagonist, a proton pump inhibitor, a prostaglandin, a radio-pharmaceutical, a hormone, a sedative, an anti-allergic agent, an appetite stimulant, an anoretic, a steroid, a sympathomimetic, a trombolytic, a thyroid agent, a vaccine, a vasodilator, a xanthine, an erectile dysfunction improvement agent, a gastrointestinal agent, a histamine receptor antagonist, a keratolytic, an antianginal agent, a non-steroidal antiinflammatory agent, a COX-2 inhibitor, a leukotriene inhibitor, a macrolide, a NSAID, a nutritional agent, an opioid analgesic, an opioid antagonist, a potassium channel activator, a protease inhibitor, an antiosteoporosis agent, an antiobesity agent, a cognition enhancer, an antiurinary incontinence agent, a nutritional oil, an antibenign prostate hypertrophy agent, an essential fatty acid, a non-essential fatty acid, a cytokine, a peptidomimetic, a peptide, a protein, a radiopharmaceutical, a senotherapeutic, a toxoid, a serum, an antibody, a nucleoside, a nucleotide, a vitamin, a portion of genetic material, a nucleic acid, or a mixture of any of these.

The biologically-active agent may also be a cytokine, a peptidomimetic, a peptide, a protein, a toxoid, a serum, an antibody, a vaccine, a nucleoside, a nucleotide, a portion of genetic material, a nucleic acid, or a mixture thereof. Non-limiting examples of therapeutic peptides/proteins are as follows: lepirudin, cetuximab, dornase alfa, denileukin diftitox, etanercept, bivalirudin, leuprolide, alteplase, interferon alfa-n1, darbepoetin alfa, reteplase, epoetin alfa, salmon calcitonin, interferon alfa-n3, pegfilgrastim, sargramostim, secretin, peginterferon alfa-2b, asparaginase, thyrotropin alfa, antihemophilic factor, anakinra, gramicidin D, intravenous immunoglobulin, anistreplase, insulin (regular), tenecteplase, menotropins, interferon gamma-1b, interferon alfa-2a (recombinant), coagulation factor Vila, oprelvekin, palifermin, glucagon (recombinant), aldesleukin, botulinum toxin Type B, omalizumab, lutropin alfa, insulin lispro, insulin glargine, collagenase, rasburicase, adalimumab, imiglucerase, abciximab, alpha-1-proteinase inhibitor, pegaspargase, interferon beta-1a, pegademase bovine, human serum albumin, eptifibatide, serum albumin iodinated, infliximab, follitropin beta, vasopressin, interferon beta-1b, hyaluronidase, rituximab, basiliximab, muromonab, digoxin immune Fab (ovine), ibritumomab, daptomycin, tositumomab, pegvisomant, botulinum toxin type A, pancrelipase, streptokinase, alemtuzumab, alglucerase, capromab, laronidase, urofollitropin, efalizumab, serum albumin, choriogonadotropin alfa, antithymocyte globulin, filgrastim, coagulation factor IX, becaplermin, agalsidase beta, interferon alfa-2b, oxytocin, enfuvirtide, palivizumab, daclizumab, bevacizumab, arcitumomab, eculizumab, panitumumab, ranibizumab, idursulfase, alglucosidase alfa, exenatide, mecasermin, pramlintide, galsulfase, abatacept, cosyntropin, corticotropin, insulin aspart, insulin detemir, insulin glulisine, pegaptanib, nesiritide, thymalfasin, defibrotide, natural alpha interferon/multiferon, glatiramer acetate, preotact, teicoplanin, canakinumab, ipilimumab, sulodexide, tocilizumab, teriparatide, pertuzumab, rilonacept, denosumab, liraglutide, golimumab, belatacept, buserelin, velaglucerase alfa, tesamorelin, brentuximab vedotin, taliglucerase alfa, belimumab, aflibercept, asparaginase erwinia chrysanthemi, ocriplasmin, glucarpidase, teduglutide, raxibacumab, certolizumab pegol, insulin isophane, epoetin zeta, obinutuzumab, fibrinolysin aka plasmin, follitropin alpha, romiplostim, lucinactant, natalizumab, aliskiren, ragweed pollen extract, secukinumab, somatotropin (recombinant), drotrecogin alfa, alefacept, OspA lipoprotein, urokinase, abarelix, sermorelin, aprotinin, gemtuzumab ozogamicin, satumomab pendetide, albiglutide, antithrombin alfa, antithrombin III (human), asfotase alfa, atezolizumab, autologous cultured chondrocytes, beractant, blinatumomab, C1 esterase inhibitor (human), coagulation factor XIII A-subunit (recombinant), conestat alfa, daratumumab, desirudin, dulaglutide, elosulfase alfa, evolocumab, fibrinogen concentrate (human), filgrastim-sndz, gastric intrinsic factor, hepatitis B immune globulin, human calcitonin, human clostridium tetani toxoid immune globulin, human rabies virus immune globulin, human Rho (D) immune globulin, human Rho(D) immune globulin, hyaluronidase (human, recombinant), idarucizumab, immune globulin (human), vedolizumab, ustekinumab, turoctocog alfa, tuberculin purified protein derivative, simoctocog alfa, siltuximab, sebelipase alfa, sacrosidase, ramucirumab, prothrombin complex concentrate, poractant alfa, pembrolizumab, peginterferon beta-1a, ofatumumab, obiltoxaximab, nivolumab, necitumumab, metreleptin, methoxy polyethylene glycol-epoetin beta, mepolizumab, ixekizumab, insulin degludec, insulin (porcine), insulin (bovine), thyroglobulin, anthrax immune globulin (human), anti-inhibitor coagulant complex, brodalumab, C1 esterase inhibitor (recombinant), chorionic gonadotropin (human), chorionic gonadotropin (recombinant), coagulation factor X (human), dinutuximab, efmoroctocog alfa, factor IX complex (human), hepatitis A vaccine, human varicella-zoster immune globulin, ibritumomab tiuxetan, lenograstim, pegloticase, protamine sulfate, protein S (human), sipuleucel-T, somatropin (recombinant), susoctocog alfa and thrombomodulin alfa.

Non-limiting examples of drugs which may be used according to the present invention are all-trans retinoic acid (tretinoin), alprazolam, allopurinol, amiodarone, amlodipine, asparaginase, astemizole, atenolol, azacitidine, azathioprine, azelatine, beclomethasone, bendamustine, bleomycin, budesonide, buprenorphine, butalbital, capecitabine, carbamazepine, carbidopa, carboplatin, cefotaxime, cephalexin, chlorambucil, cholestyramine, ciprofloxacin, cisapride, cisplatin, clarithromycin, clonazepam, clozapine, cyclophosphamide, cyclosporin, cytarabine, dacarbazine, dactinomycin, daunorubicin, diazepam, diclofenac sodium, digoxin, dipyridamole, divalproex, dobutamine, docetaxel, doxorubicin, doxazosin, enalapril, epirubicin, erlotinib, estradiol, etodolac, etoposide, everolimus, famotidine, felodipine, fentanyl citrate, fexofenadine, filgrastim, finasteride, fluconazole, flunisolide, fluorouracil, flurbiprofen, fluralaner, fluvoxamine, furosemide, gemcitabine, glipizide, gliburide, ibuprofen, ifosfamide, imatinib, indomethacin, irinotecan, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, mercaptopurine, mesna, methotrexate, methylprednisolone, midazolam, mitomycin, mitoxantrone, moxidectine, mometasone, nabumetone, naproxen, nicergoline, nifedipine, norfloxacin, omeprazole, oxaliplatin, paclitaxel, phenyloin, piroxicam, procarbazine, quinapril, ramipril, risperidone, rituximab, sertraline, simvastatin, sulindac, sunitinib, temsirolimus, terbinafine, terfenadine, thioguanine, trastuzumab, triamcinolone, valproic acid, vinblastine, vincristine, vinorelbine, zolpidem, or pharmaceutically acceptable salts of any of these. A preferred biologically active agent is azacitidine.

Compositions of the invention may comprise benzodiazipines, such as alprazomal, chlordiazepoxide, clobazam, clorazepate, diazepam, estazolam, flurazepam, lorazepam, oxazepam, quazepam, temazepam, triazolam and pharmaceutically acceptable salts of any of these.

Anaesthetics that may also be employed in the compositions of the invention may be local or general. Local anaesthetics that may be mentioned include amylocaine, ambucaine, articaine, benzocaine, benzonatate, bupivacaine, butacaine, butanilicaine, chloroprocaine, cinchocaine, cocaine, cyclomethycaine, dibucaine, diperodon, dimethocaine, eucaine, etidocaine, hexylcaine, fomocaine, fotocaine, hydroxyprocaine, isobucaine, levobupivacaine, lidocaine, mepivacaine, meprylcaine, metabutoxycaine, nitracaine, orthocaine, oxetacaine, oxybuprocaine, paraethoxycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tolycaine, tropacocaine or pharmaceutically acceptable salts of any of these.

Psychiatric drugs may also be employed in the compositions of the invention. Psychiatric drugs that may be mentioned include 5-HTP, acamprosate, agomelatine, alimemazine, amfetamine, dexamfetamine, amisulpride, amitriptyline, amobarbital, amobarbital/secobarbital, amoxapine, amphetamine(s), aripiprazole, asenapine, atomoxetine, baclofen, benperidol, bromperidol, bupropion, buspirone, butobarbital, carbamazepine, chloral hydrate, chlorpromazine, chlorprothixene, citalopram, clomethiazole, clomipramine, clonidine, clozapine, cyclobarbital/diazepam, cyproheptadine, cytisine, desipramine, desvenlafaxine, dexamfetamine, dexmethylphenidate, diphenhydramine, disulfiram, divalproex sodium, doxepin, doxylamine, duloxetine, enanthate, escitalopram, eszopiclone, fluoxetine, flupenthixol, fluphenazine, fluspirilen, fluvoxamine, gabapentin, glutethimide, guanfacine, haloperidol, hydroxyzine, iloperidone, imipramine, lamotrigine, levetiracetam, levomepromazine, levomilnacipran, lisdexamfetamine, lithium salts, lurasidone, melatonin, melperone, meprobamate, metamfetamine, nethadone, methylphenidate, mianserin, mirtazapine, moclobemide, nalmefene, naltrexone, niaprazine, nortriptyline, olanzapine, ondansetron, oxcarbazepine, paliperidone, paroxetine, penfluridol, pentobarbital, perazine, pericyazine, perphenazine, phenelzine, phenobarbital, pimozide, pregabalin, promethazine, prothipendyl, protriptyline, quetiapine, ramelteon, reboxetine, reserpine, risperidone, rubidium chloride, secobarbital, selegiline, sertindole, sertraline, sodium oxybate, sodium valproate, sodium valproate, sulpiride, thioridazine, thiothixene, tianeptine, tizanidine, topiramate, tranylcypromine, trazodone, trifluoperazine, trimipramine, tryptophan, valerian, valproic acid in 2.3:1 ratio, varenicline, venlafaxine, vilazodone, vortioxetine, zaleplon, ziprasidone, zolpidem, zopiclone, zotepine, zuclopenthixol and pharmaceutically acceptable salts of any of these.

Opioid analgesics that may be employed in compositions of the invention include buprenorphine, butorphanol, codeine, fentanyl, hydrocodone, hydromorphone, meperidine, methadone, morphine, nomethadone, opium, oxycodone, oxymorphone, pentazocine, tapentadol, tramadol and pharmaceutically acceptable salts of any of these.

Opioid antagonists that may be employed in compositions of the invention include naloxone, nalorphine, niconalorphine, diprenorphine, levallorphan, samidorphan, nalodeine, alvimopan, methylnaltrexone, naloxegol, 6β-naltrexol, axelopran, bevenopran, methylsamidorphan, naldemedine, preferably nalmefeme and, especially, naltrexone, as well as pharmaceutically acceptable salts of any of these.

Anticancer agents that may be included in compositions of the invention include the following: actinomycin, afatinib, all-trans retinoic acid, amsakrin, anagrelid, arseniktrioxid, axitinib, azacitidine, azathioprine, bendamustine, bexaroten, bleomycin, bortezomib, bosutinib, busulfan, cabazitaxel, capecitabine, carboplatin, chlorambucil, cladribine, clofarabine, cytarabine, dabrafenib, dacarbazine, dactinomycin, dasatinib, daunorubicin, decitabine, docetaxel, doxifluridine, doxorubicin, epirubicin, epothilone, erlotinib, estramustin, etoposide, everolimus, fludarabine, fluorouracil, gefitinib, guadecitabine, gemcitabine, hydroxycarbamide, hydroxyurea, idarubicin, idelalisib, ifosfamide, imatinib, irinotecan, ixazomib, kabozantinib, karfilzomib, krizotinib, lapatinib, lomustin, mechlorethamine, melphalan, mercaptopurine, mesna, methotrexate, mitotan, mitoxantrone, nelarabin, nilotinib, niraparib, olaparib, oxaliplatin, paclitaxel, panobinostat, pazopanib, pemetrexed, pixantron, ponatinib, procarbazine, regorafenib, ruxolitinib, sonidegib, sorafenib, sunitinib, tegafur, temozolomid, teniposide, tioguanine, tiotepa, topotecan, trabektedin, valrubicin, vandetanib, vemurafenib, venetoklax, vinblastine, vincristine, vindesine, vinflunin, vinorelbine, vismodegib, as well as pharmaceutically acceptable salts of any of these.

Such compounds may be used in any one of the following cancers: adenoid cystic carcinoma, adrenal gland cancer, amyloidosis, anal cancer, ataxia-telangiectasia, atypical mole syndrome, basal cell carcinoma, bile duct cancer, Birt-Hogg Dube, tube syndrome, bladder cancer, bone cancer, brain tumor, breast cancer (including breast cancer in men), carcinoid tumor, cervical cancer, colorectal cancer, ductal carcinoma, endometrial cancer, esophageal cancer, gastric cancer, gastrointestinal stromal tumor, HER2-positive, breast cancer, islet cell tumor, juvenile polyposis syndrome, kidney cancer, laryngeal cancer, acute lymphoblastic leukemia, all types of acute lymphocytic leukemia, acute myeloid leukemia, adult leukemia, childhood leukemia, chronic lymphocytic leukemia, chronic myeloid leukemia, liver cancer, lobular carcinoma, lung cancer, small cell lung cancer, Hodgkin's lymphoma, non-Hodgkin's lymphoma, malignant glioma, melanoma, meningioma, multiple myeloma, myelodysplastic syndrome, nasopharyngeal cancer, neuroendocrine tumor, oral cancer, osteosarcoma, ovarian cancer, pancreatic cancer, pancreatic neuroendocrine tumors, parathyroid cancer, penile cancer, peritoneal cancer, Peutz-Jeghers syndrome, pituitary gland tumor, polycythemia vera, prostate cancer, renal cell carcinoma, retinoblastoma, salivary gland cancer, sarcoma, Kaposi sarcoma, skin cancer, small intestine cancer, stomach cancer, testicular cancer, thymoma, thyroid cancer, uterine (endometrial) cancer, vaginal cancer, Wilms' tumor.

Other drugs that may be mentioned for use in compositions of the invention include immunomodulatory imide drugs, such as thalidomide and analogues thereof, such as pomalidomide, lenalidomide and apremilast, and pharmaceutically acceptable salts of any of these. Other drugs that many be mentioned include angiotensin II receptor type 2 agonists, such as Compound 21 (C21; 3-[4-(1H-imidazol-1-ylmethyl)phenyl]-5-(2-methylpropyl)thiophene-2-[(N-butyloxylcarbamate)-sulphonamide] and pharmaceutically acceptable (e.g. sodium) salts thereof.

According to a fourth aspect of the invention there is provided a pharmaceutical composition comprising a pharmacologically-effective amount of a biologically active agent in the form of a plurality of particles as described hereinabove, wherein the coating is configured to enable a therapeutically effective controlled or delayed release of the drug from the pharmaceutical composition obtainable by a process as hereinbefore described.

According to a fifth aspect of the invention there is provided a pharmaceutical or veterinary formulation comprising a pharmaceutical composition as described hereinabove and a pharmaceutically-acceptable or veterinary-acceptable adjuvant, diluent or carrier.

Pharmaceutical compositions as described hereinbefore (hereinafter "compositions of the invention") comprise a pharmacologically-effective amount of biologically-active agent. The term "pharmacologically-effective amount" refers to an amount of such active ingredient, which is capable of conferring a desired physiological change (such as a therapeutic effect) on a treated patient, whether administered alone or in combination with another active ingredient. Such a biological or medicinal response, or such an effect, in a patient may be objective (i.e. measurable by some test or marker) or subjective (i.e. the subject gives an indication of, or feels, an effect), and includes at least partial alleviation of the symptoms of the disease or disorder being treated, or curing or preventing said disease or disorder.

Doses of active ingredients that may be administered to a patient should thus be sufficient to affect a therapeutic response over a reasonable and/or relevant timeframe. One skilled in the art will recognize that the selection of the exact dose and composition and the most appropriate delivery regimen will also be influenced by not only the nature of the active ingredient, but also inter alia the pharmacological properties of the formulation, the route of administration, the nature and severity of the condition being treated, and the physical condition and mental acuity of the recipient, as well as the age, condition, body weight, sex and response of the patient to be treated, and the stage/severity of the disease, as well as genetic differences between patients.

Administration of compositions of the invention may be continuous or intermittent (e.g. by bolus injection). Dosages of active ingredients may also be determined by the timing and frequency of administration.

In any event, the medical practitioner, or other skilled person, will be able to determine routinely the actual dosage of any particular active ingredient, which will be most suitable for an individual patient.

Alternatively, compositions as described herein may also comprise, instead of (or in addition to) biologically-active agents, diagnostic agents (i.e. agents with no direct therapeutic activity per se, but which may be used in the diagnosis of a condition, such as a contrast agent for bioimaging).

Non-biologically active adjuvants, diluents and carriers that may be employed in cores to be coated in accordance with the invention may include pharmaceutically-acceptable substances that are soluble in water, such as carbohydrates, e.g. sugars, such as lactose and/or trehalose, and sugar alcohols, such as mannitol, sorbitol and xylitol; or pharmaceutically-acceptable inorganic salts, such as sodium chloride. Preferred carrier/excipient materials include sugars and sugar alcohols. Such carrier/excipient materials are particularly useful when the biologically active agent is a complex macromolecule, such as a peptide, a protein or portions of genetic material or the like, for example as described generally and/or the specific peptides/proteins described hereinbefore.

Compositions of the invention may be administered locally, topically or systemically, for example orally (enterally), by injection or infusion, intravenously or intraarterially (including by intravascular or other perivascular devices/dosage forms (e.g. stents)), intramuscularly, intraosseously, intracerebrally, intracerebroventricularly, intrasynovially, intrasternally, intrathecally, intralesionally, intracranially, intratumorally, cutaneously, intracutaneous, subcutaneously, transmucosally (e.g. sublingually or buccally), rectally, transdermally, nasally, pulmonarily (e.g. by inhalation, tracheally or bronchially), topically, or by any other parenteral route such as subcutaneously, intramuscular, optionally in the form of a pharmaceutical (or veterinary) preparation comprising the compound in a pharmaceutically (or veterinarily) acceptable dosage form.

The incorporation of compositions of the invention into pharmaceutical formulations may be achieved with due regard to the intended route of administration and standard pharmaceutical practice. Pharmaceutically acceptable excipients, such as carriers may be chemically inert to the biologically-active agent and may have no detrimental side effects or toxicity under the conditions of use. Such pharmaceutically acceptable carriers may also impart an immediate, or a modified, release of compositions of the invention.

Pharmaceutical (or veterinary) formulations comprising compositions of the invention may include particles of different types, for example particles comprising different active ingredients, comprising different functionalization (as described hereinbefore), particles of different sizes, and/or different thicknesses of the coatings, or a combination thereof. By combining, in a single pharmaceutical formulation, particles with different coating thicknesses and/or different core sizes, the drug release following administration to patient may be controlled (e.g. varied or extended) over a specific time period.

For peroral administration (i.e. administration to the gastrointestinal tract by mouth with swallowing), compositions of the invention may be formulated in a variety of dosage forms. Pharmaceutically acceptable carriers or diluents may be solid or liquid. Solid preparations include granules (in which granules may comprise some or all of the plurality of particles of a composition of the invention in the presence of e.g. a carrier and other excipients, such as a binder and pH adjusting agents), compressed tablets, pills, lozenges, capsules, cachets, etc. Carriers include materials that are well known to those skilled in the art, including those disclosed hereinbefore in relation to the formulation of biologically active agents within cores, as well as magnesium carbonate, pectin, dextrin, starch, gelatin, tragacanth, methylcellulose, sodium carboxymethylcellulose, a low melting wax, cocoa butter, lactose, microcrystalline cellulose, low-crystalline cellulose, and the like.

Solid dosage forms may comprise further excipients, such as flavouring agents, lubricants, binders, preservatives, disintegrants, and/or an encapsulating material. For example, compositions of the invention may be encapsulated e.g. in a soft or hard shell capsule, e.g. a gelatin capsule.

Compositions of the invention formulated for rectal administration, which may include suppositories that may contain, for example, a suitable non-irritating excipient, such as cocoa butter, synthetic glyceride esters or polyethylene glycols, which are solid at ordinary temperatures, but which liquefy and/or dissolve in the rectal cavity to release the particles of the compositions of the invention.

For parenteral administration, such as subcutaneously and intramuscular injections, the compositions of the invention may be in the form of sterile injectable and/or infusible dosage forms, for example, sterile aqueous or oleaginous suspensions of compositions of the invention.

Such suspensions may be formulated in accordance with techniques that are well known to those skilled in the art, by employing suitable dispersing or wetting agents (e.g. Tweens, such as Tween 80), and suspending agents.

Non-toxic parenterally-acceptable diluents also include solutions of 1,3-butanediol, mannitol, Ringer's solution, isotonic sodium chloride solution, sterile, fixed oils (including any bland fixed oil, such as synthetic mono- or diglycerides). Fatty acids, such as oleic acid and its glyceride derivatives may be used in the preparation of injectable formulations, as well as natural pharmaceutically-acceptable oils, such as olive oil or castor oil, and their polyoxyethylated versions and pH adjusting agents. These oil suspensions may also contain a long-chain alcohol diluent or dispersant.

Compositions of the invention suitable for injection may also comprise compositions in the form of a liquid, a sol or a gel (e.g. hyaluronic acid), which is administrable via a surgical administration apparatus, e.g. a needle, a catheter or the like, to form a depot formulation. The use of compositions of the invention may control the dissolution rate and the pharmacokinetic profile by reducing any burst effect as hereinbefore defined and/or by increasing the length of release of biologically active ingredient from that formulation.

Compositions of the invention may also be formulated for inhalation, e.g. as an inhalation powder for use with a dry powder inhaler (see, for example, those described by Kumaresan et al, *Pharma Times,* 44, 14 (2012) and Mack et al., *Inhalation,* 6, 16 (2012), the relevant disclosures thereof are hereby incorporated by reference. Suitable particle sizes for the plurality of particles in a composition of the invention for use in inhalation to the lung are in the range of about 2 to about 10 µm.

Compositions of the invention may also be formulated for administration topically to the skin, or to a mucous membrane. For topical application, the pharmaceutical formulations may be provided in the form of e.g. a lotion, a gel, a paste, a tincture, a transdermal patch, a gel for transmucosal delivery, all of which may comprise a composition of the invention. The composition may also be formulated with a suitable ointment containing a composition of the invention suspended in a carrier, such as a mineral oil, liquid petroleum, white petroleum, propylene glycol, polyoxyethylene polyoxypropylene compound, emulsifying wax or water. Suitable carrier for lotions or creams include mineral oils, sorbitan monostearate, polysorbate 60, cetyl esters wax, cetaryl alcohol, 2-octyldodecanol, benzyl alcohol and water.

Pharmaceutical formulations may comprise between about 1% to about 99%, such as between about 10% (such as about 20%, e.g. about 50%) to about 90% by weight of the composition of the invention, with the remainder made up by pharmaceutically acceptable excipients.

In any event, compositions of the invention, may be formulated with conventional pharmaceutical additives and/or excipients used in the art for the preparation of pharmaceutical formulations, and thereafter incorporated into various kinds of pharmaceutical preparations and/or dosage forms using standard techniques (see, for example, Lachman et al, "*The Theory and Practice of Industrial Pharmacy*", Lea & Febiger, 3$^{rd}$ edition (1986); "*Remington: The Science and Practice of Pharmacy*", Troy (ed.), University of the Sciences in Philadelphia, 21$^{st}$ edition (2006); and/or "*Aulton's Pharmaceutics: The Design and Manufacture of Medicines*", Aulton and Taylor (eds.), Elsevier, 4$^{th}$ edition, 2013), and the documents referred to therein, the relevant disclosures in all of which documents are hereby incorporated by reference. Otherwise, the preparation of suitable formulations may be achieved non-inventively by the skilled person using routine techniques.

Wherever the word "about" is employed herein, for example in the context of amounts (e.g. concentrations, dimensions (sizes and/or weights), size ratios, aspect ratios, proportions or fractions), temperatures or pressures, it will be appreciated that such variables are approximate and as such may vary by ±15%, such as ±10%, for example ±5% and preferably ±2% (e.g. ±1%) from the numbers specified herein. This is the case even if such numbers are presented as percentages in the first place (for example "about 15%" may mean ±15% about the number 10, which is anything between 8.5% and 11.5%).

Compositions of the invention allow for the formulation of a large diversity of pharmaceutically active compounds. Compositions of the invention may be used to treat effectively a wide variety of disorders depending on the biologically active agent that is included.

Compositions of the invention may provide a release and/or pharmacokinetic profile that minimizes any burst effect, which is characterised by a concentration maximum shortly after administration.

The compositions and processes described herein may have the advantage that, in the treatment of a relevant condition with a particular biologically active agent, they may be more convenient for the physician and/or patient than, be more efficacious than, be less toxic than, have a broader range of activity than, be more potent than, produce fewer side effects than, or that it may have other useful pharmacological properties over, any similar treatments that may be described in the prior art for the same active ingredient.

BRIEF DESCRIPTION OF THE FIGURES

Preferred embodiments of the invention will now be described, by way of non-limiting examples, with reference to the accompanying drawings in which.

DETAILED DESCRIPTION

Figure 1A:
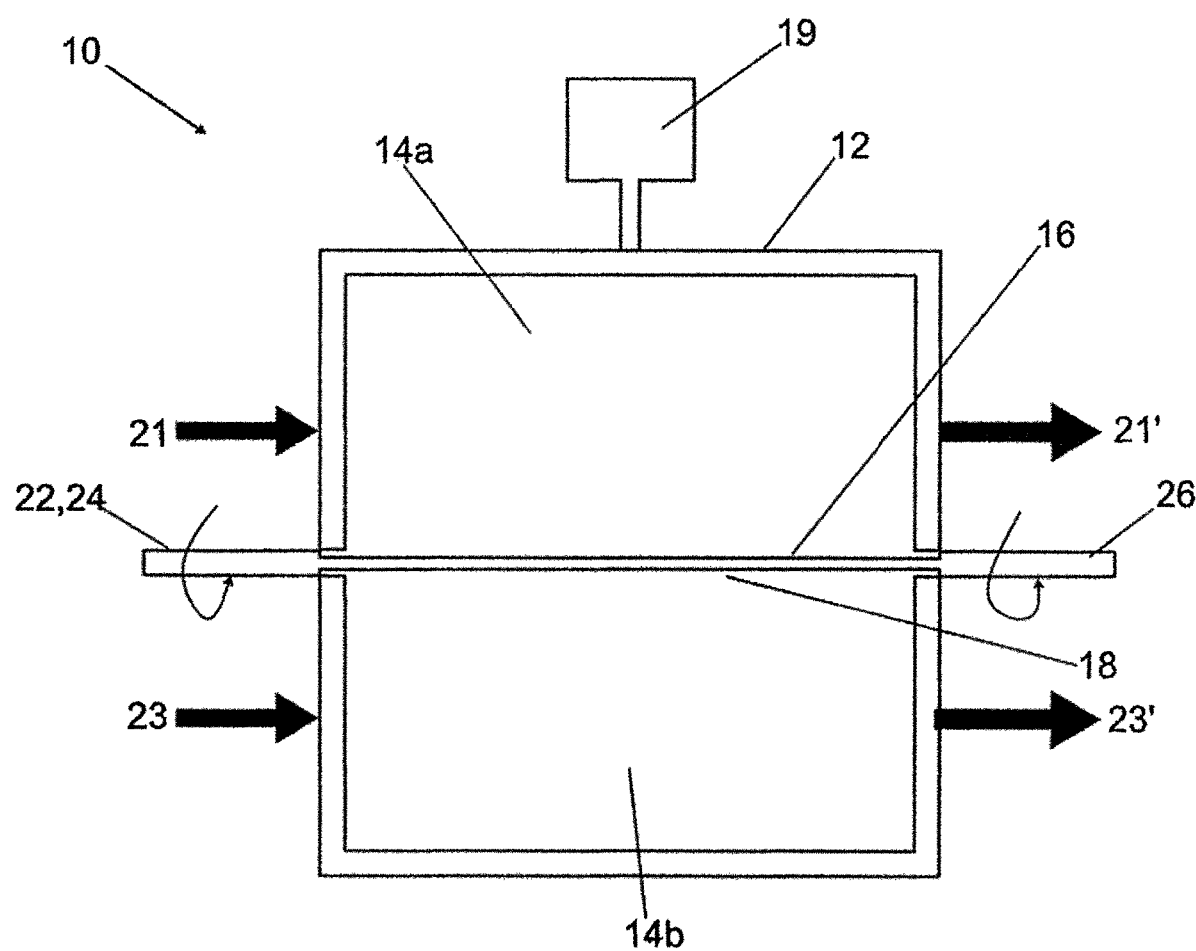
FIGS. 1*a* and 1*b* show schematic views of a reactor according to a first embodiment of the invention.

A reactor according to a first embodiment of the invention is shown in FIG. 1*a* and is designated generally by reference numeral 10.

The reactor 10 includes a reactor vessel 12 which has first and second reactor chambers 14*a*, 14*b*. In the embodiment shown, the first and second reactor chambers 14*a*, 14*b* are positioned as "upper" and "lower" chambers relative to the reactor 10. However, it is appreciated that the orientation of the first and second reactor chambers 14*a*, 14*b* may mean that they cannot be designated with such relative terms.

The reactor 10 is able to receive particles, e.g. via an inlet (not shown) into the first (i.e. upper) reactor chamber 14*a*. As previously stated in the application, the particles are preferably nanoparticles or, more preferably, microparticles. In the examples given below, the particles are typically in powder form.

The reactor 10 also includes a sieve 16 which is located inside the reactor vessel 12 between the first and second reactor chambers 14*a*, 14*b*. More specifically, in this embodiment, the sieve 16 is located on an intermediate surface 18 between the first and second reactor chambers 14*a*, 14*b*. The intermediate surface 18 being the surface which divides the first and second reactor chambers 14*a*, 14*b*.

Figure 1B:
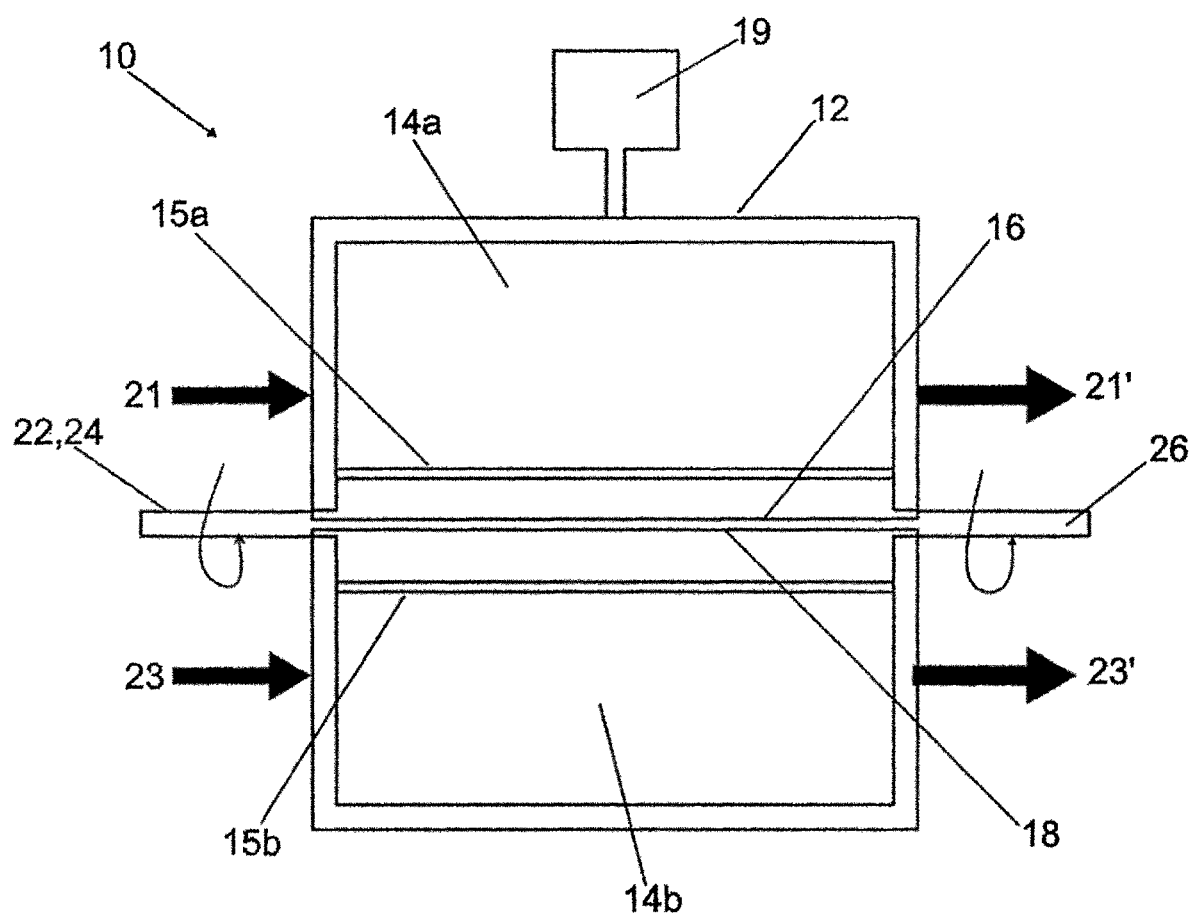

As shown in FIG. 1*b* the reactor vessel 12 may include first and second shutters 15*a*, 15*b* located immediately above and below the sieve 16. The shutters can be controlled between an open position and a closed position so as to selectively act as a physical barrier (or stop) to the particles moving between the reactor chambers 14a, 14b and vice versa.

In other embodiments of the invention, instead of shutters being used to stop the particles moving between the reactor chambers 14a, 14b, a pressured air flow may instead be used to keep the particles in a desired reactor chamber 14a, 14b.

The reactor 10 further includes a forcing means 19 which is configured to force the particles through the sieve 16. In this embodiment, it is intended that the forcing means 19 is a generator which causes physical vibration of the reactor vessel 12 via a mechanical pulse. The forcing means 19 can also be located in the intermediate space 18.

Other suitable forcing means 19 may be used. For example, a sonic or ultrasonic generator may be used to produce high-frequency vibrations which are transmitted to the reactor vessel 12 and/or the sieve 16 itself. Alternatively, or in addition, a vertical air jet may be applied to the bottom of the sieve 16 surface and at the same time a vacuum acts in the opposite direction to the air jet so that the air jet deagglomerates the particles while the vacuum pulls the deagglomerated particles down through the sieve 16. Alternatively, or in addition, the reactor vessel 12 or reactor chambers 14a, 14b may be subjected to fast rotation so as to provide centrifugal force to the particles as they contact the sieve 16, thus causing deagglomeration. The forcing means 19 may instead be the shaking movement caused by tumbling/rotating of the first and second reactor chambers 14a, 14b. Alternatively, the forcing means may be a vibration that are introduced to the reactor chambers 14a, 14b by "punches" or "tapping" imparted on the chambers 14a, 14b and/or the sieve 16 by, e.g. a solenoid, (or other means of physically "punching" or "tapping" the chambers 14a, 14b and/or sieve 16). Alternatively, the forcing means 19 may be caused by oscillating the chambers 14a, 14b and/or the sieve 16. The forcing means 19 may instead be a pressure gradient force applied to the sieve 16 surface. Alternatively, the forcing means 19 may be the force applied due to horizontal rotation, e.g. of the sieve 16 and/or the chambers 14a, 14b. The forcing means 19 may instead be the force applied from periodic displacement/motion of the sieve 16.

Any suitable combination of one or more of the forcing means discussed above may be used. Exemplary combinations (which are non-limiting) include: oscillating and tapping, rotating and tapping, ultrasonic vibration and sonic vibration, sonic vibration and tapping, ultrasonic vibration and tapping, horizontal rotation and period displacement. The combination may be chosen to achieve the desired deagglomeration and/or to combine different functionalities of the forcing means. For example, ultrasonic vibration may be chosen to help clean the sieve 16 which may be combined with another forcing means to move the particles through the sieve 16.

Although not shown in the figures, the forcing means 19 may include a forcing aid. The forcing aid may be any one or a combination of the following:

Brush cleaning with one or more brushes which brush over the sieve 16 to help break up particle aggregates, the brush(es) may sweep along the sieve surface 16 in a circular motion via an arm;

Bouncing ball cleaning with a plurality of balls, e.g. hard 2 mm balls, that are bounced on the sieve surface to help break up particle aggregates;

Air jet cleaning with a fan to blow air or gas into a central cavity and then out of jet arms which are aimed towards the sieve, the air jet may reach speeds of up to 120 m/s Use of a scraper, spatula or paddle in a similar manner to that described above in relation to brush cleaning, with the scraper/spatula/paddle typically being made from rubber.

The reactor 10 also includes a gas phase coating mechanism which is configured to introduce pulses of gas phase materials into one or both of the reactor chambers 14a, 14b so as to form a coating on the particles.

In the embodiment shown, the gas phase coating mechanism incorporates an atomic layer deposition (ALD) technique, although other related techniques may instead be used.

The general ALD technique is described in the introductory part of the application. The reaction chamber of an ALD process is under vacuum, typically 1 to 20 mbar for thermal ALD, although lower or higher pressures can be used. The temperature in the vacuum chamber is also well controlled and may typically be in the range of 20-300° C., although lower or higher temperatures can be used.

It can be typical to have some dislocation of the substrate in the ALD reaction chamber, for example rotating or tumbling or shaking of the chamber so as to keep the substrate moving during the process. However, the substrate, particularly particles (e.g. powder), is not forced through a sieve nor deagglomerated by such dislocation techniques. Instead, the particles are simply moved around in the reaction chamber.

With reference to the reactor 10 of the first embodiment of the invention, the gas phase coating mechanism applies ALD technique according to the following steps:

a) Pulse 1: Introducing a first precursor in a gaseous state into the reactor chamber 14a, 14b which contains the particles to be coated. The precursor is adsorbed onto the surface of the particles to form an adsorbed (e.g. chemisorbed) layer of precursor molecule on all surfaces exposed to the gas. For example, the first precursor may be $H_2O$ in a gaseous state. The water terminates the surface with hydroxy (—OH) groups.

b) Pulse 2: Introducing chemically inert rinse gas (e.g. $N_2$ or Ar) to the reactor chamber 14a, 14b to rinse the reactor chamber 14a, 14b of excess of the first precursor. The excess also includes ligands from the precursor that detach from the precursor molecule when it adsorbs to the surface. All that remains on the particles is a monolayer of the first precursor.

c) Pulse 3: Introducing a second precursor in a gaseous state into the reactor chamber 14a, 14b which contains the particles to be coated. The precursor reacts with the adsorbed first precursor to form a new substance (i.e. a new layer of a different chemical composition than before) which coats the particles. For example, the new substance that is formed on the particles may be aluminium oxide ($Al_2O_3$).

d) Pulse 4: Introducing a chemically inert rinse gas (e.g. $N_2$ or Ar) to the reactor chamber 14a, 14b to rinse the reactor chamber 14a, 14b of excess of the second precursor and ligands from the precursor that detach from the precursor molecule when it adsorbs to the surface and any by-products from the reaction between the first and second precursors. All that remains on the particles is essentially a monolayer of the reaction product, e.g. $Al_2O_3$.

The four pulses described above represent a so-called "ALD cycle", which can be repeated several times as an "ALD set". For example, an ALD set may consist of 10, 25 or 100 cycles.

An ALD pulse can in consist of many pulses, e.g. a pulse may be repeated 2-1000 times with purging or evacuation in between. A set of repeating ALD pulses are referred to as multipulses.

The skilled person would readily understand the components required to carry out such an ALD technique, as well as the interface of such components with the reactor vessel 12, and so such components are not discussed here.

In the first embodiment, an ALD cycle is performed in the first (upper) reactor chamber 14*a*, and so the appropriate ALD gases, i.e. precursor and rinse gases, would be introduced as pulses through an upper inlet 21 and out through an upper outlet 21' at the first reactor chamber 14*a*. Alternatively the appropriate precursor and rinse gases can instead be introduced as pulses through an upper inlet 23 and out through a lower outlet 23' at the second (lower) reactor chamber 14*b*.

The forcing means 19 is configured to force the particles through the sieve 16 in use, and the sieve 16 is configured to deagglomerate any particle aggregates formed in the reactor vessel 12. The ratio of the size of particles to the sieve mesh size may be 1:2. For example, for particle sizes in the region of 10 μm, a 20 μm sieve mesh could be used. The ratio of the size of particles to the sieve mesh size may be 1:4. For example, for particle sizes in the region of 5 μm, a 20 μm sieve mesh could also be used.

The sieve 16 may take any suitable form. For example, the sieve 16 may have a sieve mesh that is made from threads or wires, e.g. it may be a woven wire sieve 16. The sieve 16 may instead be in the form of a perforated plate sieve, a microplate sieve, a grid sieve or a diamond sieve.

The reactor 10 further includes a particle position changing means 22, in the form of a movement member 24. The movement member 24 has an axle 26 secured to the reactor vessel 12 which is rotated so as to rotate the whole reactor vessel 12 along the axis of the axle 26 (i.e. the horizontal axis in the example shown). Rotation of the reactor vessel 12 results in the first and second reactor chambers 14*a*, 14*b* switching places with one another. In other words, the reactor chamber 14*a*, 14*b* which was the upper chamber becomes the lower chamber and vice versa. In this way, the particles are moved from one physical space in the reactor 10, e.g. the space of the lower chamber before rotation, to another physical space in the reactor 10, e.g. to the space of the upper chamber after rotation.

The reactor 10 may further include anti-static electricity prevention equipment. Such equipment may be included within the reactor 10 at suitable locations, such as within the reactor chambers 14*a*, 14*b*, so as to remove static energy from the particles and/or parts of the reactor 10.

In use, particles, in this case a powder, are introduced to the first (upper) reactor chamber 14*a*. The ALD process coats the particles using one ALD cycle. The ALD gases are introduced to the upper chamber 14*a* through the upper inlet 21 and extracted through the upper outlet 21'. The ALD gases can also be extracted from the lower outlet 23' in the second (lower) reactor chamber 14*b*. The particles are forced through the sieve 16 by the vibration caused by the generator of the forcing means 19, so that the particles are forced into the second (lower) reactor chamber 14*b*.

The reactor vessel 12 can also include first and second shutters 15*a*, 15*b* located immediately above and below the sieve 16, as shown in FIG. 1*b*. The shutters 15*a*, 15*b* can be controlled between an open position and a closed position so as to selectively act as a physical barrier (or stop) to the particles moving between the reactor chambers 14*a*, 14*b*.

In use, the shutters 15*a*, 15*b* are in a closed position during the ALD process and are opened prior to forcing the particles through the sieve 16. Particles that have aggregated together during the ALD process are deagglomerated by the forcible sieving. These particles will have pinholes of uncoated surface area such that the core (what was the original particle) may be exposed.

In both of the examples shown in FIGS. 1*a* and 1*b*, the movement member 24 then rotates the reactor vessel 12 along the movement member axle 26 so that the reactor chambers 14*a*, 14*b* switch places. The second reactor chamber 14*b*, which was the lower chamber, that contains the coated particles is now located as the upper chamber in the reactor 10. The ALD process is then repeated. These steps may be repeated any number of times to achieve fully coated particles. The steps may also be repeated a further number of times to achieve the desired thickness of coating.

In other embodiments of the invention, an ALD set (i.e. several ALD cycles) may be performed to the particles in the reactor chamber 14*a*, 14*b* before rotation of the reactor chambers 14*a*, 14*b* is carried out. Thus, the particles are forced through the sieve (and therefore deagglomeration is performed) after every ALD set.

In further embodiments, a single pulse is performed to the particles in the reactor chamber 14*a*, 14*b* before rotation of the reactor chambers 14*a*, 14*b* is carried out. Thus, the particles are forced through the sieve (and therefore deagglomeration is performed) after each pulse.

In any event, the fully coated particles with the desired coating thickness are finally removed from the reactor vessel 12 by an outlet (not shown) or by disassembling the reactor 12.

It may be necessary (depending upon how the particles are initially provided) to wash and/or clean them to remove impurities that may derive from their production, and then dry them before carrying out the steps outlined above. Drying may be carried out by way of numerous techniques known to those skilled in the art, including evaporation, spray-drying, vacuum drying, freeze drying, fluidized bed drying, microwave drying, IR radiation, drum drying, etc. If dried, the particles may then be deagglomerated by grinding, screening, milling and/or dry sonication. Alternatively, the particles may be treated to remove any volatile materials that may be absorbed onto its surface, e.g. by exposing the particle to vacuum and/or elevated temperature.

Surfaces of the particles may be chemically activated prior to applying the first inorganic coating, e.g. by treatment with hydrogen peroxide, ozone, free radical-containing reactants or by applying a plasma treatment, in order to create free oxygen radicals at the surface of the particle. This in turn may produce favourable adsorption/nucleation sites on the particles for the ALD precursors.

In ALD, coatings may be applied at process temperatures from about 0° C. to about 800° C., or from about 40° C. to about 200° C., e.g. from about 40° C. to about 150°, such as from about 30° C. to about 100° C. The optimal process temperature depends on the reactivity of the precursors and/or the substances (including biologically-active agents) that are employed in the particles and/or melting point and/or vapor pressure of the particle substance(s).

In most instances, the first of the consecutive reactions will involve some functional group or free electron pairs or radicals at the surface to be coated, such as a hydroxy group (—OH) or a primary or secondary amino group (—$NH_2$ or —NHR where R e.g. is an aliphatic group, such as an alkyl group). The individual reactions are advantageously carried out separately and under conditions such that all excess reagents and reaction products are essentially removed before conducting the subsequent reaction.

Figure 2:
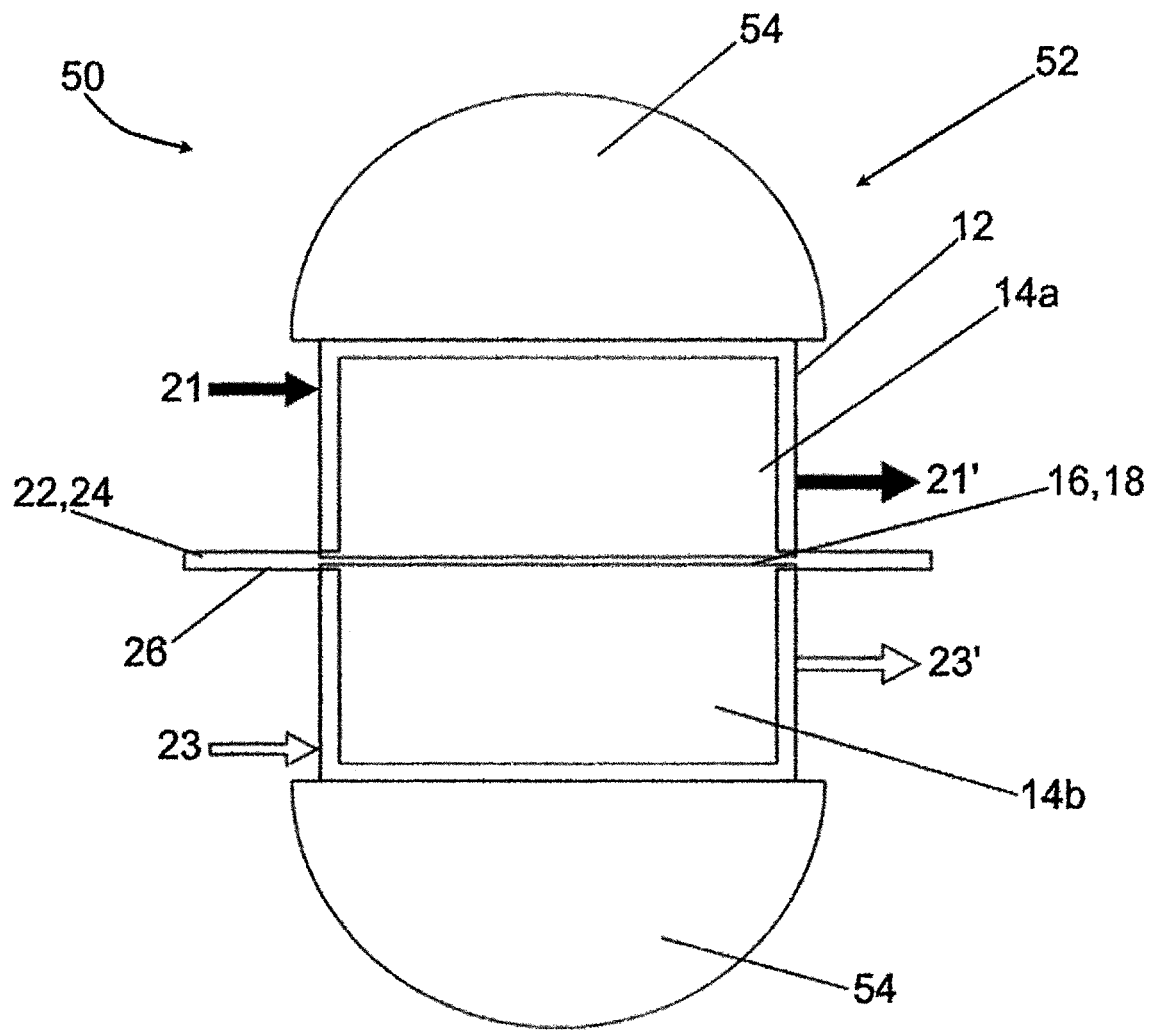
FIG. 2 shows a schematic view of a reactor according to a second embodiment of the invention.

A reactor according to a second embodiment of the invention is shown in FIG. 2 and is designated generally by reference numeral 50.

The reactor 50 of the second embodiment of the invention is similar to the reactor 10 of the first embodiment of the invention, and like features share the same reference numerals.

The reactor 50 of the second embodiment differs from the reactor 10 of the first embodiment in that the forcing means 52 is integrated with the reactor vessel 12 such that the vessel 12 and sieve 16 act as a sonic sifter. In particular, the top of the first (upper) reactor chamber 14a and the bottom of the second (lower) reactor chamber 14b is fabricated from a polymeric material, preferably an elastomer, to form a polymer membrane 54. Moreover, the sieve 16 is also fabricated from a polymeric material, preferably an elastomer. Sound waves or ultrasonic sound waves are applied to the reactor vessel 12 via a generator (not shown) such that the whole vessel 12 acts as a sonic sifter with the sound travelling through the polymer membranes 54 and polymer sieve 16.

Operation of the reactor 50 of the second embodiment is the same as the reactor 10 of the first embodiment, but with the mechanical pulse being replaced with the sonic sifter as outlined above.

Figure 3A:
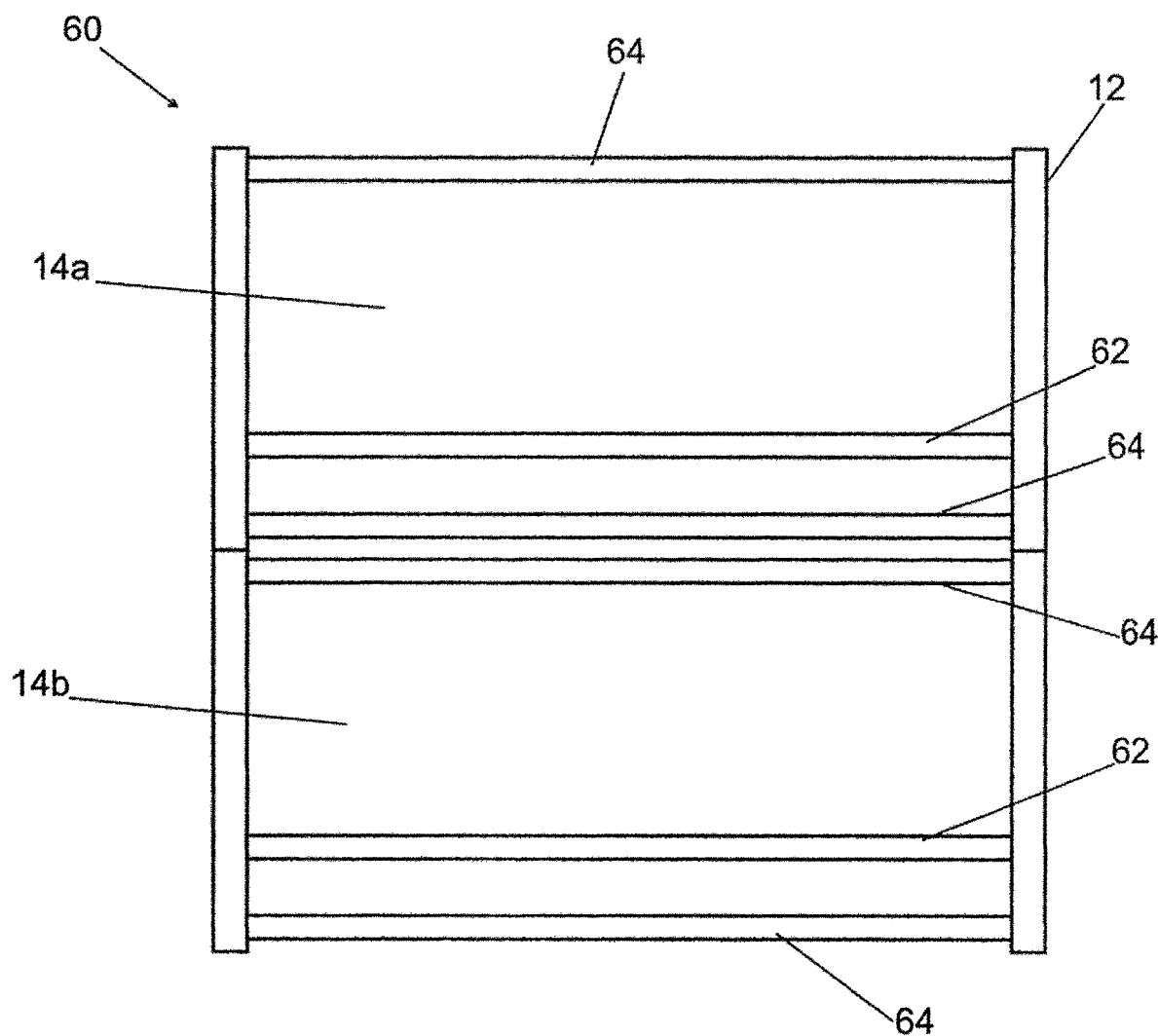
FIG. 3*a* shows a schematic view of a reactor according to a third embodiment of the invention.
Figure 3B:
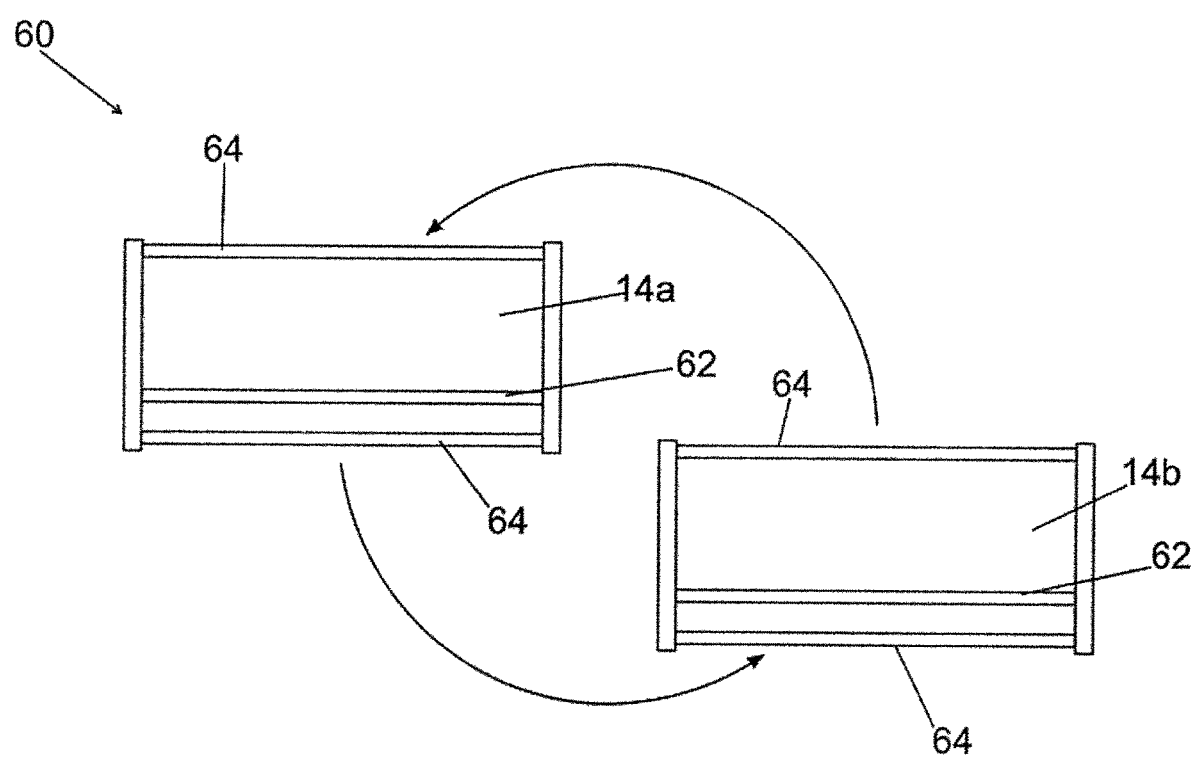
FIG. 3*b* shows the reactor of FIG. 3*a* as the chambers are switching places.

A reactor according to a third embodiment of the invention is shown in FIGS. 3a and 3b and is designated generally by reference numeral 60.

The reactor 60 of the third embodiment of the invention is similar to the reactor 10 of the first embodiment of the invention, and like features share the same reference numerals.

The reactor 60 of the third embodiment differs from the reactor 10 of the first embodiment in that each of the first and second reactor chambers 14a, 14b has a sieving surface 62 which is made from a sieve mesh. The sieving surface 62 is located towards the bottom end of each first and second reactor chamber 14a, 14b.

Moreover, each of the first and second reactor chambers 14a, 14b has a shutter surface 64 both at the top and bottom surfaces of the chambers 14a, 14b, so that when the reactor chambers 14a, 14b are switched places with one another (as described in more detail below), there is always a shutter surface 64 of each chamber 14a, 14b located between the chambers 14a, 14b.

The movement member (not shown in FIG. 3a or 3b) is configured to switch places of the first and second chambers 14a, 14b without rotation. For example, the movement member may remove each of the chambers 14a, 14b out of line with one another and insert them back into line with one another in the opposite order, as indicated by FIG. 3b. The movement member in such an embodiment may do this simultaneously or sequentially.

In contrast to the first embodiment reactor 10 in which the reactor chambers 14a, 14b form a single, integrated unit, the first and second reactor chambers 14a, 14b of the second embodiment reactor 60 are individual, discrete chambers (as shown in FIG. 3b).

Operation of the reactor 60 of the third embodiment is the same as the reactor 10 of the first embodiment, but with the movement member switching places of the first and second reactor chambers 14a, 14b without rotation. Moreover, the shutter surfaces 64 of each chamber 14a, 14b that are positioned between the two chambers 14a, 14b are controlled to be in an opened position when the particles are being forced through the sieve 62, and are controlled to be in a closed position when the reactor chambers 14a, 14b are being switched places.

Figure 4:
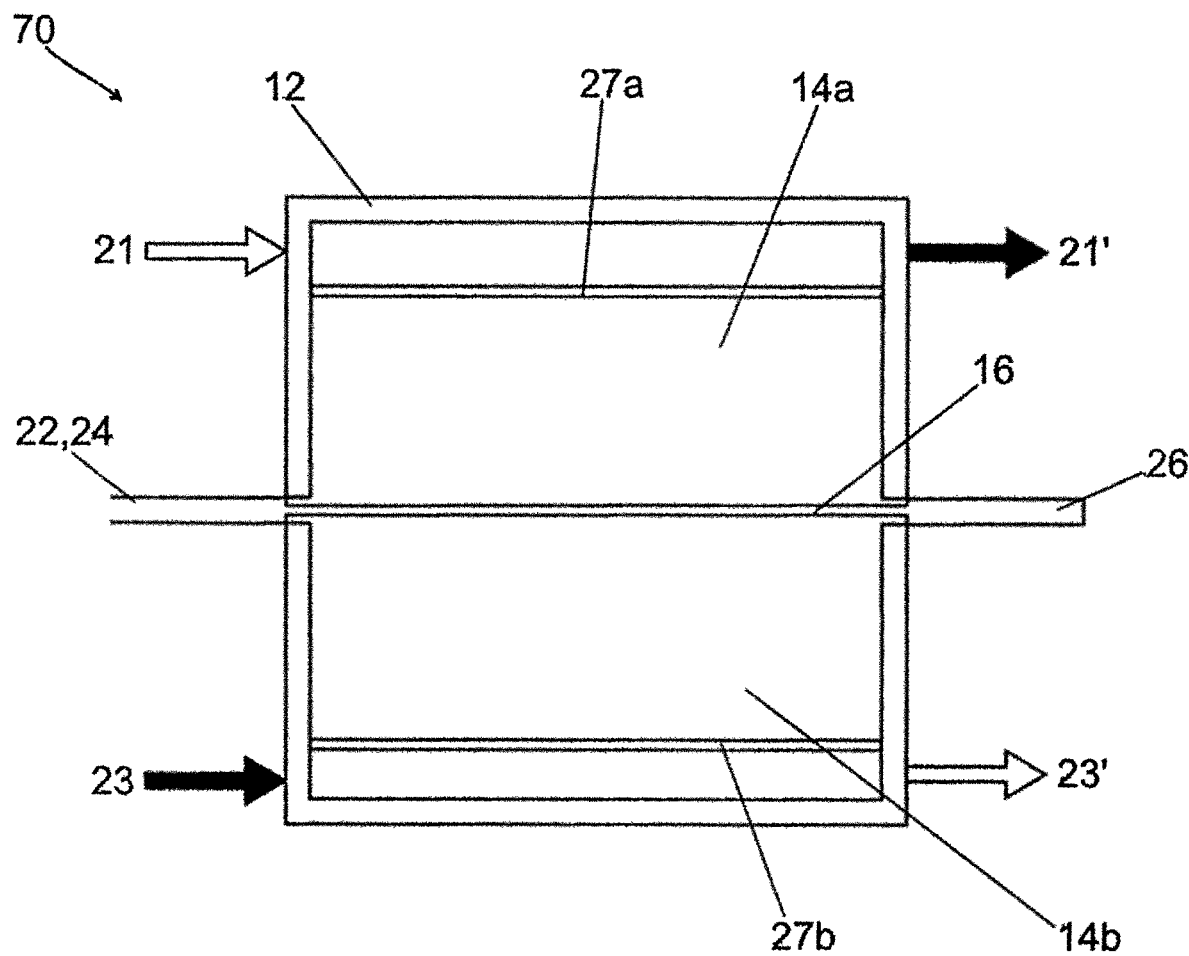
FIG. 4 shows a schematic view of a reactor according to a fourth embodiment of the invention.

A reactor according to a fourth embodiment of the invention is shown in FIG. 4 and is designated generally by reference numeral 70.

The reactor 70 of the fourth embodiment of the invention is similar to the reactor 10 of the first embodiment of the invention, and like features share the same reference numerals.

The reactor 70 of the fourth embodiment differs from the reactor 10 of the first embodiment in that the first and second chambers 14a, 14b each include respective first and second secondary sieves 27a, 27b. The mesh size of each secondary sieve 27a, 27b may be smaller than the size of the particles being introduced into the reactor 12.

The ALD process (a pulse, cycle or set) is performed in the second (lower) chamber 14b. The particles are placed on the second (lower) secondary sieve 27b and ALD gases are introduced through the lower inlet 23 and extracted through the lower outlet 23' or through the upper outlet 21' in the same way as in the first embodiment.

The reactor 70 can then be rotated to switch places of the reactor chambers 14a, 14b (or otherwise switched places without rotation, as described in relation to the third embodiment), and the ALD process is repeated. The particles are forced through the second (lower) secondary sieve 27b by a forcing means (not shown) either before or after the reactor 70 is rotated, depending on the nature of rotation of the reactor 70. The particles are then also forced through the sieve 16, which lies between the reactor chambers 14a, 14b by a forcing means so that the particles are moved from one chamber to the other 14a, 14b (as described in the previous embodiments).

This process is repeated until fully coated particles with a desired coating thickness are achieved.

Any suitable forcing means as previously described could be used for forcing of the particles through the secondary sieves 27a, 27b.

In other embodiments of the invention, the particle position changing means is a particle transport mechanism which is configured to transport the particles from the second (lower) chamber 14b to the first (upper) chamber 14a after ALD has been carried out in the second (lower) chamber 14b. In this way, the reactor chambers 14a, 14b themselves do not need to be moved (rotated or otherwise).

A reactor according to a fifth embodiment of the invention is shown in FIGS. 5a to 5d and is designated generally by reference numeral 80.

The reactor 80 of the fifth embodiment of the invention is similar to the reactor 10 of the first embodiment of the invention, and like features share the same reference numerals.

The reactor 80 of the fifth embodiment differs from the reactor 10 of the first embodiment in that it includes a selective gas flow means 82 to form a particle bed flow 84 in each reactor chamber 14a, 14b in turn.

Figure 5A:
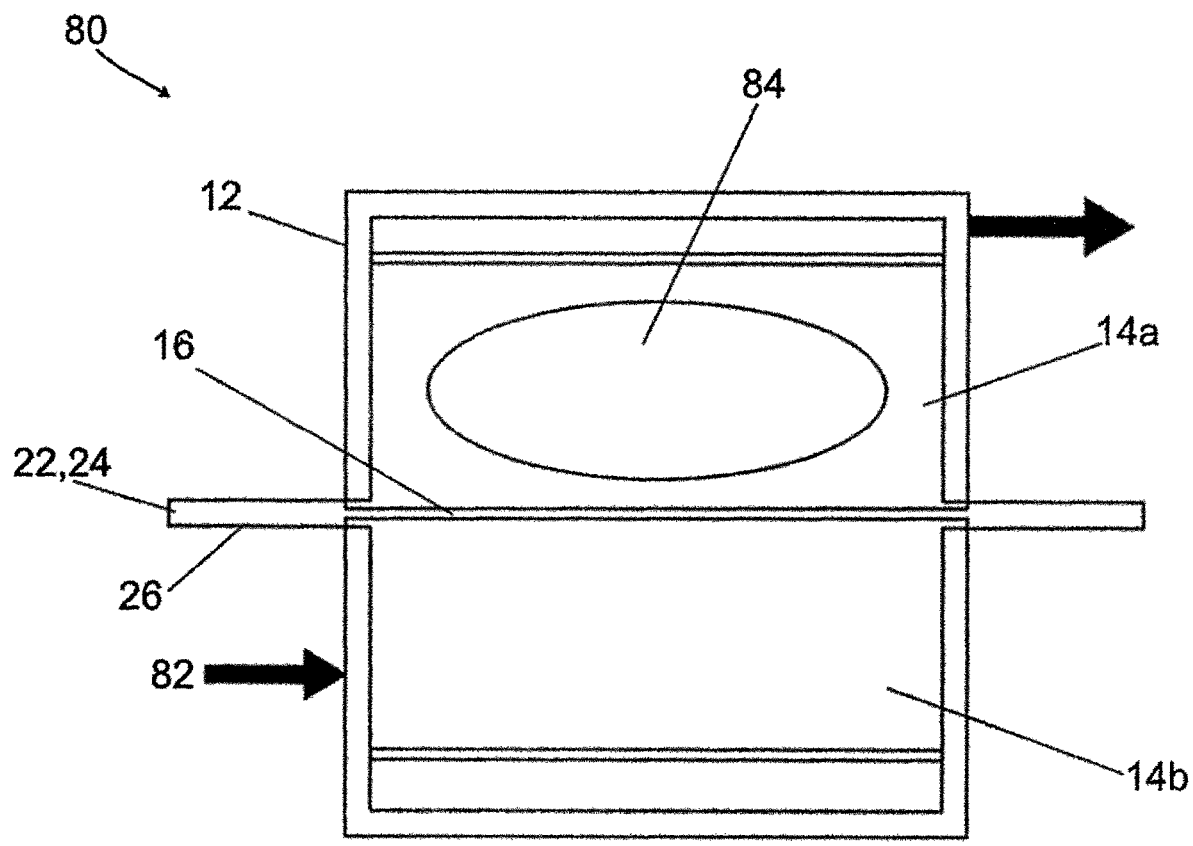
FIGS. 5*a* to 5*d* show schematic views of a reactor according to a fifth embodiment of the invention.

In particular, the gas flow means 82 provides a flow of gas at a high pressure from the second (lower) reactor chamber 14b to the first (upper) reactor chamber 14a, which forms a "flowing" particle bed 84, as would be found on a flushbed, in the first (upper) reactor chamber 14a. In other words, the gas flow means 82 keeps the floating particles 84 in the first (upper) reactor chamber 14a, as shown in FIG. 5a.

An ALD set, cycle or pulse can be performed in the first (upper) reactor chamber 14a while the particles are being held in place by the gas flow means 82.

Figure 5B:
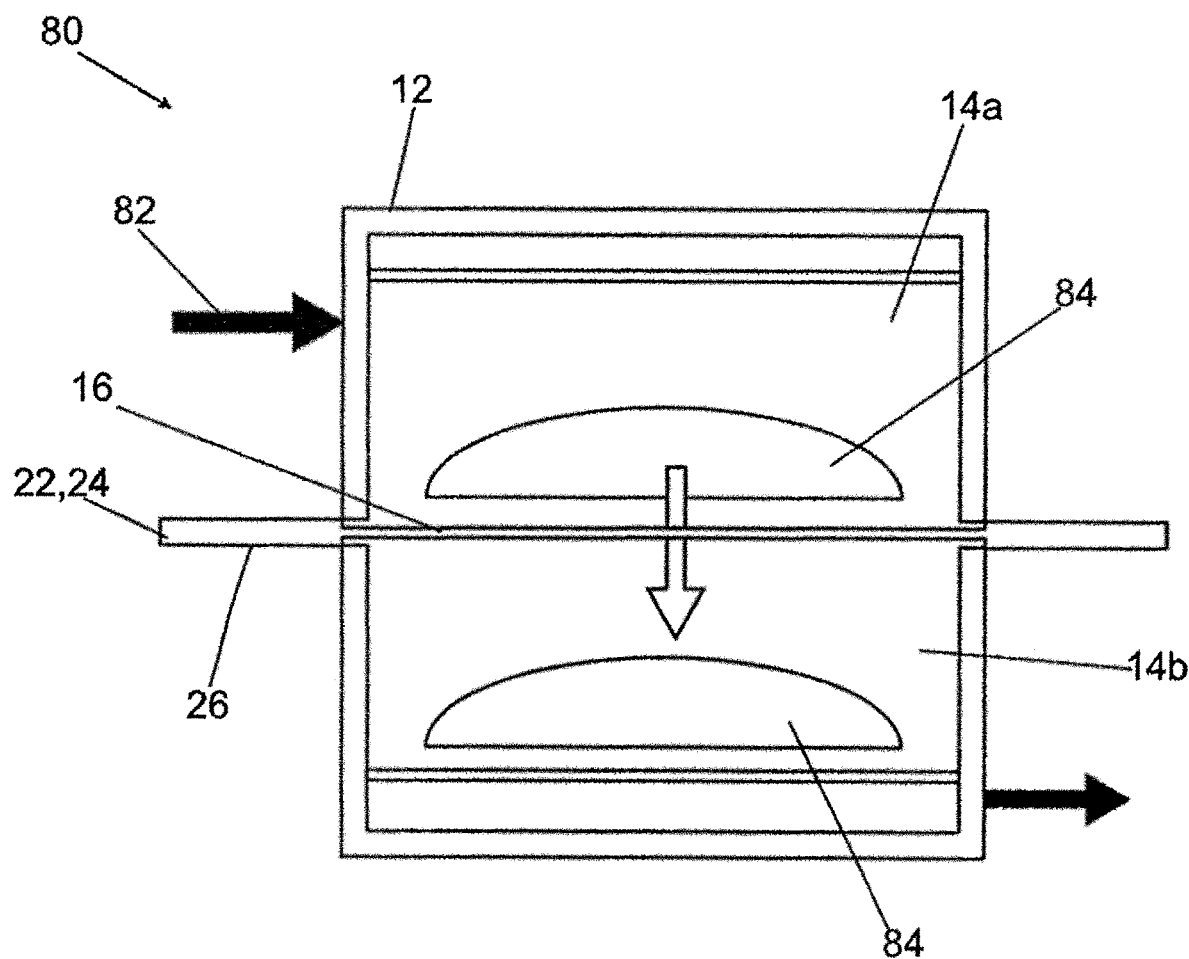

The gas flow means 82 switches to provide a flow of gas at high pressure from the first (upper) reactor chamber 14a to the second (lower) reactor chamber 14b. The gas flow means 82 are thereafter switched off and the particle bed 84 is therefore pushed through the sieve 16, which deagglomerates any aggregate particles formed during the ALD process. This step is shown in FIG. 5b.

The particles being forced through the sieve 16 by the gas flow may be aided by vibrations to the reactor vessel 12 (e.g. physical, sonic, ultrasonic). As mentioned previously, a forcing aid may also be used, such as balls, brushes, paddles etc.

Figure 5C:
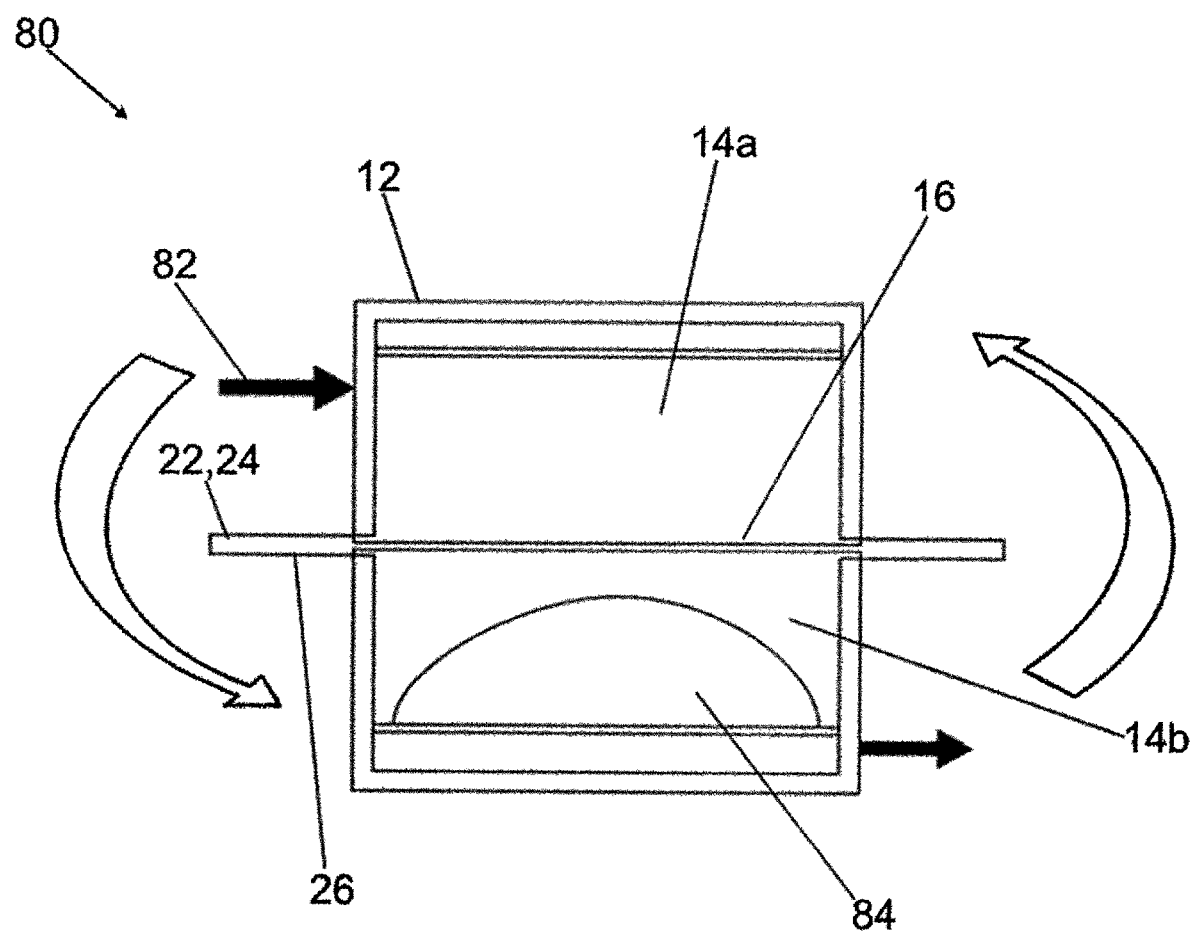

The flowing particle bed 84 is now in the second (lower) chamber, as shown in FIG. 5c. As indicated in FIG. 5c, the reactor chambers 14a, 14b are then rotated, in the same manner as described above in relation to the first embodiment of the invention, so that the reactor chambers 14a, 14b switch places.

Figure 5D:
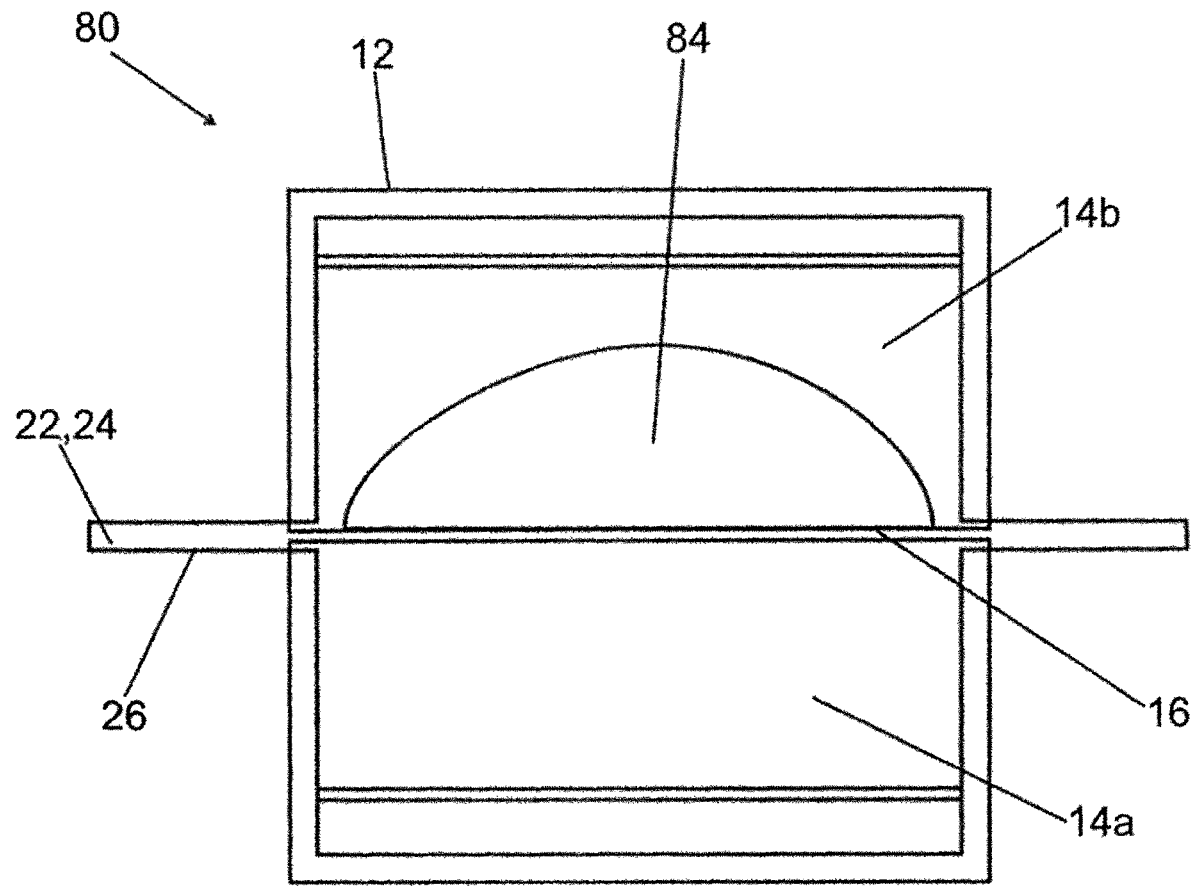

The flowing particle bed 84 is still in the second chamber 14b, but the second reactor chamber 14b is now the upper chamber, as shown in FIG. 5d.

The ALD process is repeated in the second (now upper) reactor chamber 14b, and the gas flow means 82 is again switched to force the particles through the sieve 16. The ALD and forced sieving steps are repeated to form fully coated particles with a desired coating thickness.

As with the reactor 10 of the first embodiment, the first and second reactor chambers 14a, 14b may instead be switched places by means other than rotation.

Moreover, in other embodiments of the invention, after the flowing particle bed 84 has been forced through the sieve 16 from the first (upper) reactor chamber 14a to the second (lower) reactor chamber 14b (i.e. after the step shown in FIG. 5b), the ALD process (i.e. an ALD set, cycle or pulse) may be performed in the second (lower) reactor chamber 14b. The gas flow means 82 may then force the flowing particle bed 84 back through the sieve 16 from the second (lower) reactor chamber 14b to the first (upper) reactor chamber 14a. the ALD process (e.g. an ALD set, cycle or pulse) may then be carried out in the first (upper) reactor chamber 14a. This process is repeated as desired. In this way, no movement of the reactor chambers 14a, 14b is needed. Moreover, the forcing means (i.e. the gas flow means 82) is the particle position changing means (i.e. a particle transport mechanism) in such an embodiment.

Figure 6:
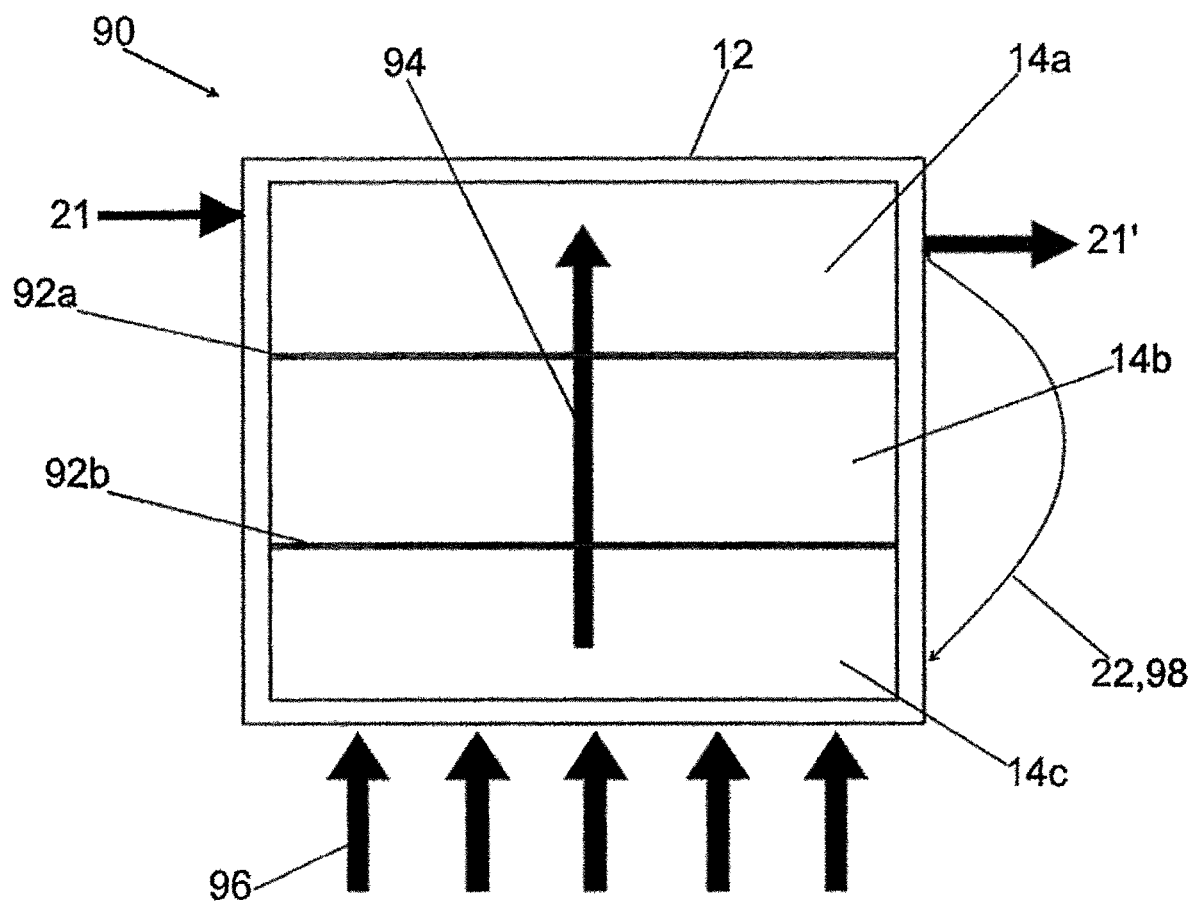
FIG. 6 shows a schematic view of a reactor according to a sixth embodiment of the invention.

A reactor according to a sixth embodiment of the invention is shown in FIG. 6 and is designated generally by reference numeral 90.

The reactor 90 of the sixth embodiment of the invention is similar to the reactor 10 of the first embodiment of the invention, and like features share the same reference numerals.

The reactor 90 of the sixth embodiment differs from the reactor 10 of the first embodiment in that it includes two sieves 92a, 92b within the reactor vessel 12. The sieves 92a, 92b are spaced from one another to form three associated reactor chambers 14a, 14b, 14c.

The sieves 92a, 92b each have a finer mesh in the direction of forcible movement 94 of the particles. In this embodiment, the upper sieve 92a has a finer sieve mesh than the lower sieve 92b since the particles are forced from the bottom of the reactor vessel 12 upwards.

In the latter regard, the reactor 90 includes a gas flow means 96 which provides high pressure gas flow from the bottom of the reactor vessel 12 so as to force the particles upwards through the lower and upper sieves 92b, 92a in turn.

In other embodiments of the invention, there may be more than two sieves 92a, 92b, each having a finer mesh in the direction of forcible movement 94 of the particles.

As shown, the gas phase coating mechanism, i.e. via an inlet 21 and outlet 21', is configured to perform an ALD process in the uppermost chamber 14a. The gas phase coating mechanism may perform an ALD set, cycle or pulse in the uppermost chamber 14a. After which time, a particle position changing means 22, in the form of a particle transport mechanism 98, transports the particles from the uppermost chamber 14a to the lowermost chamber 14c. The gas flow means 96 then forces the particles again up through the sieves 92a, 92b. This deagglomeration is carried out after each ALD set, cycle or pulse.

This process is repeated until the particles are fully enclosed in the coating and the coating has a desired thickness.

Figure 7:
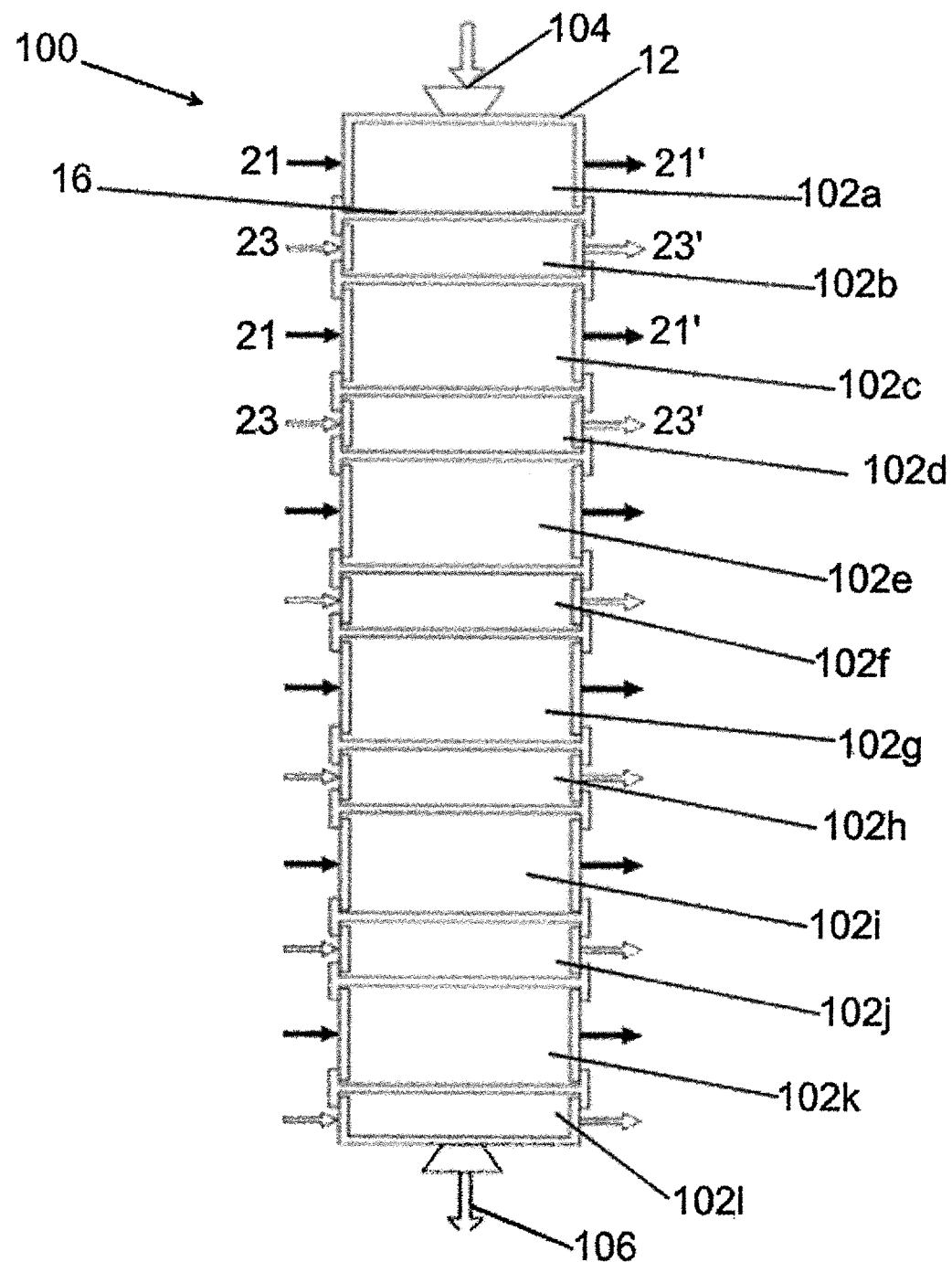
FIG. 7 shows a schematic view of a reactor according to a seventh embodiment of the invention.

A reactor according to a seventh embodiment of the invention is shown in FIG. 7 and is designated generally by reference numeral 100.

The reactor 100 of the seventh embodiment of the invention is similar to the reactor 10 of the first embodiment of the invention, and like features share the same reference numerals.

The reactor 100 of the seventh embodiment differs from the reactor 10 of the first embodiment in that it includes a plurality of reactor chambers 102a, 102b, 102c . . . 102l stacked together in a tower configuration. In this embodiment there are 12 reactor chambers 102a-102l with a sieve 16 positioned between each neighbouring chamber 102a-102l.

In this embodiment, each reactor chamber 102a-102l performs an ALD pulse, and the particles are forced through each sieve 16 in turn after each pulse. Thus, deagglomeration is carried out between each pulse of an ALD cycle.

The particles are forced through each sieve 16 by the forcing means (not shown) which may be any suitable form as already described in this application.

As a further explanation, the gas phase coating mechanism, i.e. via the inlet 21 and outlet 21', at the first reactor chamber 102a introduces the first precursor (e.g. $H_2O$ in gaseous form), i.e. pulse 1. The forcing means, e.g. a sonic sifter, forces the partially coated particles through the neighbouring sieve 16 and into the second reactor chamber 102b. The gas phase coating mechanism, i.e. via the inlet 23 and outlet 23', at the second reactor chamber 102b introduces the rinse gas (e.g. $N_2$) to rinse the reaction chamber and particles from excess of the first precursor, i.e. pulse 2. The forcing means again forces the partially coated particles through the next neighbouring sieve 16 and into the third reactor chamber 102c. The gas phase coating mechanism 21, 21' at the third reactor chamber 102c introduces the second precursor, i.e. pulse 3. The forcing means once again forces the coated particles through the neighbouring sieve 16 and into the fourth reactor chamber 102d. The gas phase coating mechanism 23, 23' at the fourth reactor chamber 102d introduces the rinse gas (e.g. $N_2$) to rinse the reactor chamber and particles of excess of the second precursor and any by-products from the reaction between the first and second precursors.

If this number of pulses, i.e. one ALD cycle, is sufficient to fully coat the particles (which is a possibility since deagglomeration is taking place every pulse) and the desired coating thickness has been reached, then the reactor 100 would include only 4 reactor chambers 102a, 102b, 102c, 102d and the fully coated particles would be removed from the fourth reactor chamber 102d. If, however, further cycles are required, then the reactor 100 would include the required further reactor chambers 102e, 102f . . . 102l (as shown in FIG. 7) and the alternating gas pulse and deagglomeration steps would be repeated.

As indicated, any number of reactor chambers 102a-102l can be added to the reactor 100 so that the alternating ALD pulse and deagglomeration process can be repeated a desired number of times. Theoretically, there could be hundreds of reactor chambers 102a-102l.

The particles are fed into the reactor 100 at an inlet 104 at the first reactor chamber 102a, and the fully coated particles exit the reactor 100 at an outlet 106 at the last reactor chamber 102l. In this way, new particles can be continuously fed into the reactor 100 at the inlet 104 while a previous batch of particles are still making their way through the reactor 100. The feed rate can be adjusted in relation to the product output at the outlet 106.

In other embodiments of the invention, each reactor chamber 102a-102k may perform more than one ALD pulse. For example, each reactor chamber 102a-102l may perform an ALD cycle (e.g. four pulses), so that deagglomeration is carried out between each ALD cycle. Alternatively, each reactor chamber 102 may perform an ALD set (e.g. 25 cycles) so that deagglomeration is carried out between each ALD set. In such embodiments, the reactor 100 may include a particle position changing means (either in the form of a movement member or a particle transport mechanism) which is configured to action movement of the particles from one reactor chamber 102 to another, thus allowing the ALD and deagglomeration process to be repeated.

For example, the reactor 100 may include four reactor chambers 102a, 102b, 102c, 102d, each of which is configured to carry out an ALD pulse with deagglomeration in between each pulse. After the four pulses have been completed (i.e. one ALD cycle), the whole reactor vessel 12 may be rotated by a movement member (in a similar manner to that described in relation to the first embodiment of the invention) so that the particles that were in the lowermost chamber are then in the uppermost chamber. The ALD pulse and deagglomeration process can then be repeated any number of times.

The invention claimed is:

1. A reactor for forming a plurality of fully coated particles having solid cores, the reactor comprising:
a reactor vessel configured to receive microparticles comprising a biologically active agent;
a gas phase coating mechanism configured to selectively introduce pulses of gas phase materials that form a coating on the microparticles;

a sieve located within the reactor vessel; and a forcing means configured to force the coated microparticles through the sieve in use, wherein the sieve is configured to deagglomerate any microparticle aggregates formed in the reactor vessel upon forcing of the microparticles by the forcing means through the sieve; and the forcing means is configured to force the coated microparticles through the sieve after at least one cycle of pulses of gas phase materials provided by the gas phase coating mechanism;

wherein the reactor vessel includes more than one reactor chamber, the sieve being located between each neighbouring reactor chamber, the gas phase coating mechanism being configured to selectively introduce one or more pulses of gas phase material to the microparticles in one or each reactor chamber; and the reactor further includes a particle position changing means configured to action movement of the microparticles from one physical space in the reactor to another to permit forcing of the coated microparticles through the sieve;

wherein the particle position changing means comprises a movement member configured to physically move each of the reactor chambers so as to switch places of the reactor chambers.

2. The reactor according to claim 1, wherein the forcing means includes: shaking, tapping, oscillating, tumbling, horizontal rotation, periodic displacement of the sieve, centrifugal force, sonic vibration, ultrasonic vibration, vacuum, air column, pressure gradient, gas flow, brushing, gravitational or a combination thereof.

3. The reactor according to claim 1, wherein the forcing means is integrated with the reactor vessel and includes ultrasonic vibration such that the vessel and sieve act as a sonic sifter.

4. The reactor according to claim 1, wherein the forcing means includes a forcing aid to aid in forcing the coated microparticles through the sieve in use.

5. The reactor according to claim 4, wherein the forcing aid includes: brush, balls, scraper, spatula, paddle, air jet, or a combination thereof.

6. The reactor according to claim 1, wherein the ratio of the size of coated microparticles to the sieve mesh size is about 1:2.

7. The reactor according to claim 1, wherein the particle position changing means is configured to action movement of the microparticles from one physical space in the reactor to another to permit subsequent forcing of the coated microparticles through the sieve.

8. The reactor according to claim 7, wherein the movement member is configured to rotate the reactor chambers along a single axis to switch places of the reactor chambers.

9. The reactor according to claim 7, wherein each reactor chamber includes a sieve located on an intermediate surface, the intermediate surface being located between neighbouring reactor chambers upon switching of their places so that a sieve is located between the reactor chambers at any given time.

10. The reactor according to claim 1, wherein the particle position changing means further comprises a particle transport mechanism configured to transport the coated microparticles between each of the reactor chambers.

11. The reactor according to claim 10, wherein the particle transport mechanism comprises a gas flow, a vacuum or a combination thereof.

12. The reactor according to claim 1, further including a stop means positioned relative to the sieve to selectively prevent passing of the microparticles through the sieve into a neighbouring reactor chamber.

13. The reactor according to claim 12, wherein the stop means includes: a physical stop, an airflow, or a combination thereof.

14. The reactor according to claim 1, wherein the forcing means is configured to force the coated microparticles through more than one sieve after each pulse between separate pluralities of pulses of gas phase materials being provided by the gas phase coating mechanism.

15. The reactor according to claim 1, wherein the forcing means is configured to force the coated microparticles through the sieve after a plurality of pulses of gas phase materials is provided by the gas phase coating mechanism.

16. The reactor according to claim 1, wherein the gas phase coating mechanism incorporates one of the following gas phase coating techniques: atomic layer deposition (ALD), atomic layer epitaxy (ALE), molecular layer deposition (MLD), molecular layer epitaxy (MLE), chemical vapor deposition (CVD), atomic layer CVD, molecular layer CVD, binary reaction sequence chemistry.

17. A reactor for forming a plurality of fully coated particles having solid cores, the reactor comprising:
- a reactor vessel configured to receive particles;
- a gas phase coating mechanism configured to selectively introduce pulses of gas phase materials that form a coating on the particles;
- a plurality of sieves located within the reactor vessel, each sieve having progressively finer meshes in the direction of forcible movement of the particles;
- forcing means configured to force the particles through the sieves in use, and
- wherein each sieve is configured to deagglomerate particle aggregates formed in the reactor vessel upon forcing of the particles through the sieve.

18. The reactor according to claim 17, wherein the reactor vessel comprises more than one reactor chamber with a sieve being located between each neighbouring reactor chamber, the gas phase coating mechanism being configured to selectively introduce one or more pulses of gas phase material to the particles in each reactor chamber.

19. The reactor according to claim 17, wherein the forcing means is configured to force the particles through the after each cycle of pulses of gas phase materials provided by the gas phase coating mechanism.

20. The reactor according to claim 17, wherein the forcing means is configured to force the particles through the sieve after a plurality of pulses of gas phase materials is provided by the gas phase coating mechanism.

21. The reactor according to claim 18, further comprising a particle position changing means configured to action movement of the particles from one physical space in the reactor vessel to another to permit subsequent forcing of the particles through at least one sieve.

22. The reactor according to claim 21, wherein the particle position changing means is a movement member configured to physically move each of the reactor chambers so as to switch places of the reactor chambers.

23. The reactor according to claim 22, wherein each reactor chamber includes a sieve located on an intermediate surface, the intermediate surface being located between neighbouring reactor chambers upon switching of their places so that a sieve is located between the reactor chambers at any given time.

24. The reactor according to claim 23, wherein the particle position changing means includes a movement member configured to physically move each of the reactor chambers so as to switch places of the reactor chambers and a particle transport mechanism configured to transport the particles between each of the reactor chambers.

25. The reactor according to claim 17, wherein the particles are microparticles comprising a biologically active agent.

26. The reactor according to claim 17, wherein the forcing means is configured to force the coated microparticles through the sieve after at least one cycle of pulses of gas phase materials provided by the gas phase coating mechanism.

* * * * *